(12) United States Patent
Crouzet et al.

(10) Patent No.: US 6,410,298 B1
(45) Date of Patent: Jun. 25, 2002

(54) ADENOVIRUS VECTORS AND METHOD FOR REDUCING HOMOLOGOUS RECOMBINATION PHENOMENA

(75) Inventors: Joel Crouzet; Jean-Jacques Robert, both of Sceaux; Emmanuelle Vigne, Ivry sur Seine; Patrice Yeh, Gif sur Yvette, all of (FR)

(73) Assignee: Aventis Pharma S.A., Antony Cedex (FR)

( * ) Notice: Subject to any disclaimer, the term of this patent is extended or adjusted under 35 U.S.C. 154(b) by 0 days.

(21) Appl. No.: 09/530,378
(22) PCT Filed: Nov. 17, 1998
(86) PCT No.: PCT/FR98/02453
§ 371 (c)(1),
(2), (4) Date: Sep. 11, 2000
(87) PCT Pub. No.: WO99/25861
PCT Pub. Date: May 27, 1999

(51) Int. Cl.$^7$ .............. C12N 7/00; C12Q 1/70; C12Q 1/68; C12P 21/06; C07H 21/02
(52) U.S. Cl. ............. 435/235.1; 435/5; 435/6; 435/69.1; 435/325; 536/23.1
(58) Field of Search .............. 435/5, 6, 69.1, 435/235.1, 325; 536/23.1

(56) References Cited

FOREIGN PATENT DOCUMENTS

| WO | WO 9613596 | 5/1996 |
|---|---|---|
| WO | WO 9630534 | 10/1996 |
| WO | WO 9700326 | 1/1997 |

OTHER PUBLICATIONS

Krougliak, Development of Cell Lines Capable of Complementing E1, E4, and Protein IX Defective Adenovirus Type 5 Mutants, Dec. 1995, vol. 6, pp. 1575–1586.

Morgenstern & Land, Advanced mammalian gene transfer: high titre retroviral vectors with multiple drug selection markers and a complementary helper–free packaging cell line, May 7, 1990, vol. 18, pp. 3587–3596.

Primary Examiner—Hankyel T. Park
(74) Attorney, Agent, or Firm—Wiley Rein & Fielding LLP

(57) ABSTRACT

The invention concerns a method for reducing recombination phenomena among nucleic acids. It also concerns the use of said method for producing defective viruses not contaminated by replication particles. The invention further concerns novel viral constructs.

19 Claims, 16 Drawing Sheets

Figure 2:
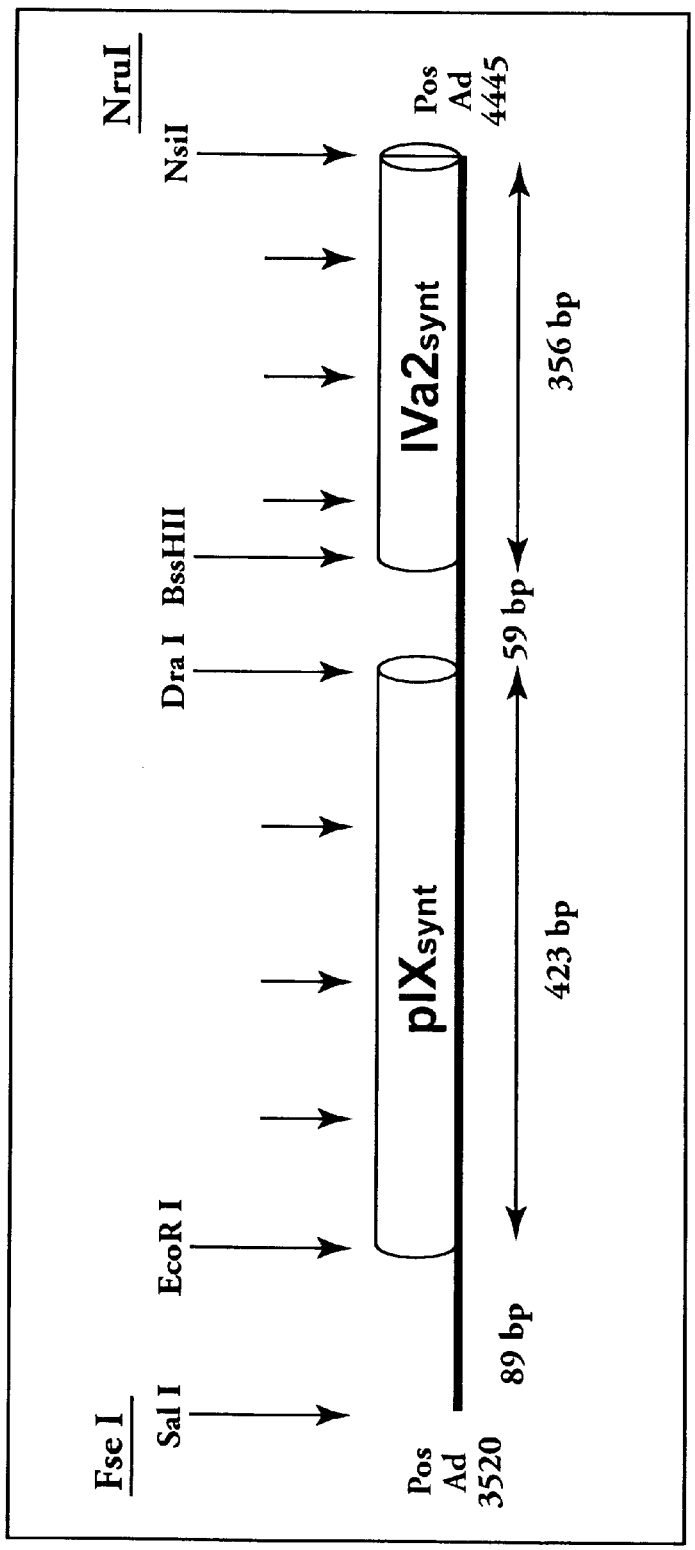

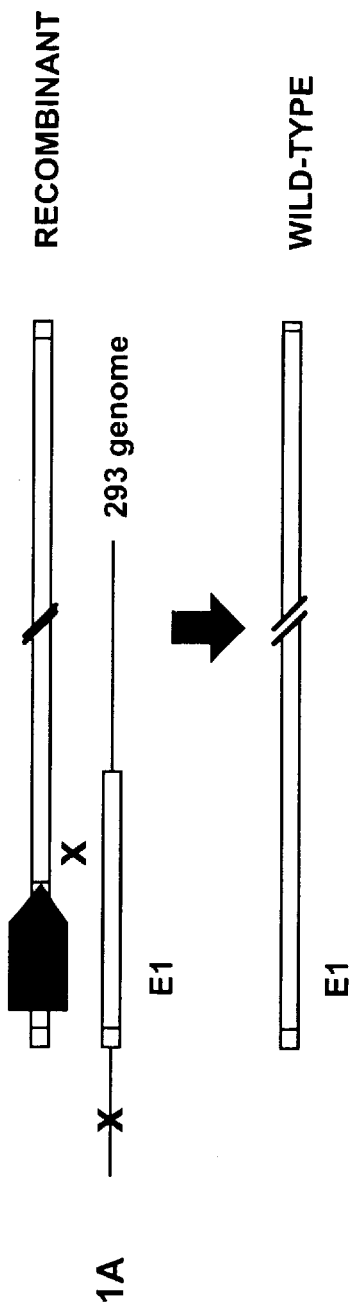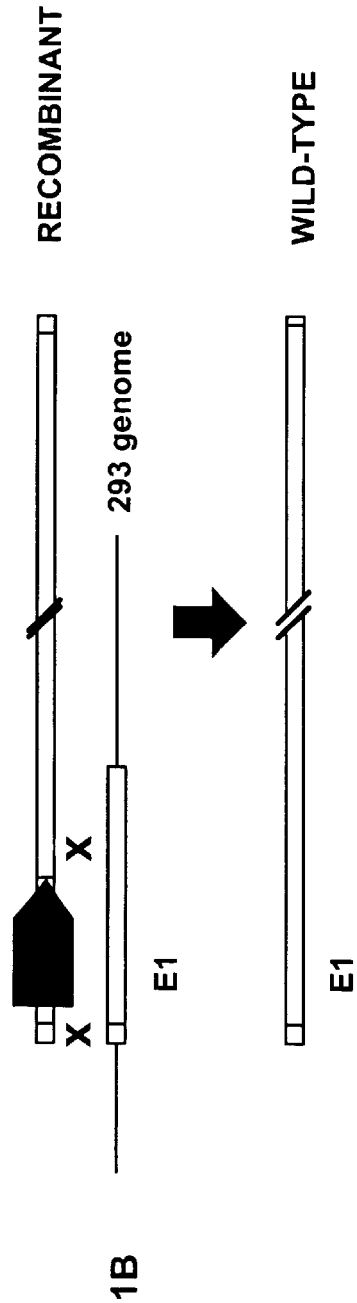
Figure 1

OLIGO-SYNGEN I -> Restriction Map

DNA sequence    44 b.p.    AACTGCAGGCCG ... CAGCCATATCCC    linear

```
            CfrI
            NgoMI
            NaeI
        FseI
     Cac8 I  SpeI
   SfcI  Cfr10 I        NruI
   PstI  Cac8 I
    ‖     ‖‖·‖      ‖     ‖·‖                                       44
AACTGCAGGCCGGCCACTAGTCGGATGTTCCCAGCCATATCCC
TTGACGTCCGGCCGGTGATCAGCCTACAAGGGTCGGGTATAGGG
   ‖     ‖‖·‖      ‖     ‖·‖
   3      9          16    21
   3      9
      5      8
             9
             9
                11
```

Figure 7A

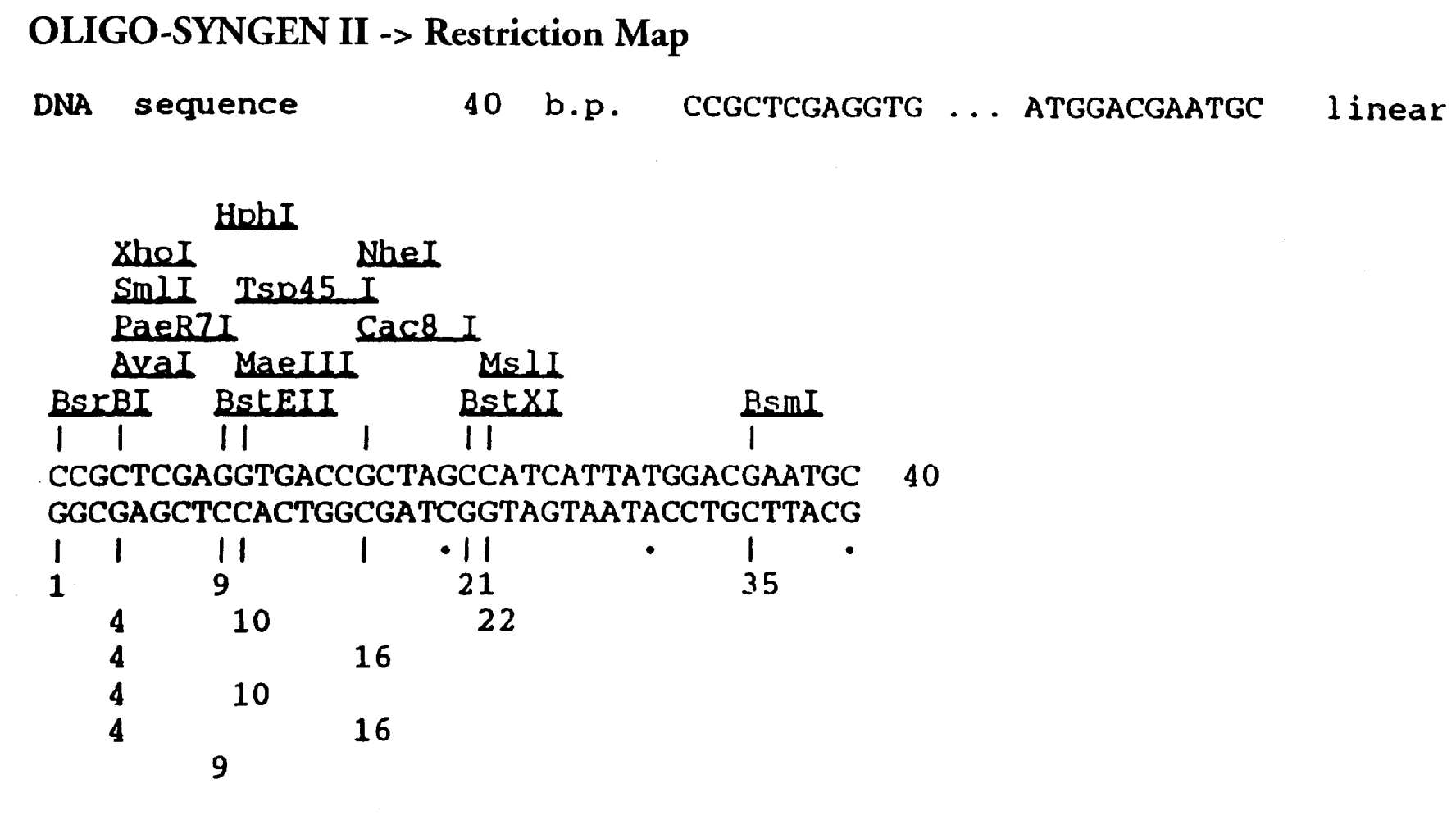

OLIGO-SYNGEN II -> Restriction Map

DNA sequence    40 b.p.    CCGCTCGAGGTG ... ATGGACGAATGC    linear

```
             HphI
      XhoI       NheI
      SmlI  Tsp45I
      PaeR7I     Cac8_I
      AvaI  MaeIII          MslI
      BsrBI BstEII          BstXI         BsmI
      |     |               |             |
      CCGCTCGAGGTGACCGCTAGCCATCATTATGGACGAATGC    40
      GGCGAGCTCCACTGGCGATCGGTAGTAATACCTGCTTACG
      |     |       |       |             |
      1     9       16      22            35
      4     10              21
      4     10
      4     11
      4     11
      1
```

Figure 7B

Degeneracy in pIX

```
1/1
ATG TCC ACG AAT TCC TTT GAC GGC TCC ATC
ATG AGC ACC AAC TCG TTT GAT GGA AGC ATT
Met ser thr asn ser phe asp gly ser ile 31/11
GTC TCC AGC TAC CTG ACC ACC CGG ATG CCT
GTG AGC TCA TAT TTG ACA ACG CGC ATG CCC
val ser ser tyr leu thr thr arg met pro 61/21
CCC TGG GCT GGC GTC CGC CAA AAC GTC ATG
CCA TGG GCC GGG GTG CGT CAG AAT GTG ATG
pro trp ala gly val arg gln asn val met 91/31
GGA AGC TCC ATC GAC GGC AGG CCT GTG CTC
GGC TCC AGC ATT GAT GGT CGC CCC GTC CTG
gly ser ser ile asp gly arg pro val leu 121/41
CCT GCC AAT AGC ACC ACT CTG ACT TAT GAA
CCC GCA AAC TCT ACT ACC TTG ACC TAC GAG
pro ala asn ser thr thr leu thr tyr glu 151/51
ACT GTC AGC GGC ACC CCA CTG GAA ACC GCC
ACC GTG TCT GGA ACG CCG TTG GAG ACT GCA
thr val ser gly thr pro leu glu thr ala 181/61
GCA AGC GCT GCA GCC AGC GCT GCC GCC GCT
GCC TCC GCC GCC GCT TCA GCC GCT GCA GCC
ala ser ala ala ala ser ala ala ala ala
```

Figure 8A

```
211/71
ACT GCT CGG GGC ATC GTC ACC GAT TTC GCC
ACC GCC CGC GGG ATT GTG ACT GAC TTT GCT
thr ala arg gly ile val thr asp phe ala 241/81
TTT CTC TCC CCT CTG GCC TCC AGC GCT GCC
TTC CTG AGC CCG CTT GCA AGC AGT GCA GCT
phe leu ser pro leu ala ser ser ala ala 271/91
AGC CGC AGC TCT GCT CGG GAC GAT AAA CTG
TCC CGT TCA TCC GCC CGC GAT GAC AAG TTG
ser arg ser ser ala arg asp asp lys leu 301/101
ACC GCC CTG CTG GCT CAG CTG GAC AGC CTG
ACG GCT CTT TTG GCA CAA TTG GAT TCT TTG
thr ala leu leu ala gln leu asp ser leu 331/111
ACT AGG GAG CTG AAC GTG GTG AGC CAA CAA
ACC CGG GAA CTT AAT GTC GTT TCT CAG CAG
thr arg glu leu asn val val ser gln gln 361/121
CTC CTG GAC CTC CGG CAA CAA GTG AGC GCT
CTG TTG GAT CTG CGC CAG CAG GTT TCT GCC
leu leu asp leu arg gln gln val ser ala 391/131
CTC AAA GCC TCT AGC CCA CCT AAC GCC GTT
CTG AAG GCT TCC TCC CCT CCC AAT GCG GTT
leu lys ala ser ser pro pro asn ala val

421/141
TAA
TAA
```

Figure 8B

Degeneracy in IVa2

```
1/1
  TC GCG AAC CTA AAA ATA CAG TCC AAG ATG
  TA GCC AAC CTA AAA ATA CAG TCC AAG ATG
ile ala asn leu lys ile gln ser lys met 31/11
CAT CTG ATA TCC CCA CGT ATG CAC CCC TCC
CAT CTC ATA TCC CCA CGT ATG CAC CCA TCC
his leu ile ser pro arg met his pro ser 61/21
CAG CTT AAC CGC TTC GTA AAC ACT TAC ACC
CAG CTT AAC CGC TTT GTA AAC ACT TAC ACC
gln leu asn arg phe val asn thr tyr thr 91/31
AAG GGA CTG CCC CTG GCA ATC AGC CTG CTA
AAG GGC CTG CCC CTG GCA ATC AGC TTG CTA
lys gly leu pro leu ala ile ser leu leu 121/41
CTG AAA GAC ATT TTC AGG CAC CAC GCC CAG
CTG AAA GAC ATT TTT AGG CAC CAC GCC CAG
leu lys asp ile phe arg his his ala gln 151/51
CGG TCC TGC TAC GAC TGG ATT ATC TAC AAC
CGC TCC TGC TAC GAC TGG ATC ATC TAC AAC
arg ser cys tyr asp trp ile ile tyr asn 181/61
ACC ACT CCG CAG CAT GAA GCT CTC CAG TGG
ACC ACC CCG CAG CAT GAA GCT CTG CAG TGG
thr thr pro gln his glu ala leu gln trp
```

Figure 9A

211/71
TGC TAC CTC CAT CCC AGA GAC GGG CTT ATG
TGC TAC CTC CAC CCC AGA GAC GGG CTT ATG
cys tyr leu his pro arg asp gly leu met 241/81
CCT ATG TAT CTG AAC ATC CAG AGC CAC CTT
CCC ATG TAT CTG AAC ATC CAG AGT CAC CTT
pro met tyr leu asn ile gln ser his leu 271/91
TAC CAC GTC CTC GAA AAA ATA CAC AGG ACC
TAC CAC GTC CTG GAA AAA ATA CAC AGG ACC
tyr his val leu glu lys ile his arg thr 301/101
CTG AAC GAC CGA GAC CGC TGG TCT CGG GCC
CTC AAC GAC CGA GAC CGC TGG TCC CGG GCC
leu asn asp arg asp arg trp ser arg ala 331/111
TAC CGC GCG CGG AAA ACC CCT AAA TAA
TAC CGC GCG CGC AAA ACC CCT AAA TAA
tyr arg ala arg lys thr pro lys OCH

Figure 9B

```
                                                                                                        560
ACAAGTGAGCGGCTCTCAAGCCCTCTAGCCCACCTAAGCCCGTTAAAACATAAATAAAAACCAGACTCTGTTTGATTT
                                                        Dra I
                                                                                                        640
GGATCAAGCAAGTGTCTTGCTGTCTTTATTTAGGAGTTTTCCGGCGGTAGCCCGAGACCAGCGGTCTCGTTC
                                                                BssH II
  PpuM I
                                                                                                        720
AGGGTCCTGTGTATTTTTCGAGGACGTGGTAAAGGTGGCTCTGGATGTTCAGATACATAGCCCGTCTCTGGG
                                                                                                        800
ATGGAGGTAGCACCACTGGAGAGCTTCATGCTGCGGAGTGTGTGTAGATAATCCAGTCGTAGCAGGACCGCTGGGCGT
  IVa2                                                          Sty I
                                                                                                        880
GGTGCCTGAAAATGTCTTTCAGTAGCAGGCTGATTGCCAGGGGCAGTCCCTGGTGTAAGTGTTTACGAAGCGGTTAAGC
                    Nsi I                                                Nru I
TGGGAGGGGTGCATACGTGGGATATGAGAGATGCATCTTGGACTGTATTTTAGGTTCGCGA   941
```

Figure 10B

Detection of RCAs after 7 successive amplifications of 5 different plaques derived from the vectors ad5p53 and AV1.7p53

- Results of expermints to detect RCAs in the samples derived from amplification No. 7. Experiments in triplicate.

|  | ad5CMVp53 | × | AV1.7CMVp53 |  |  |  |  |
|---|---|---|---|---|---|---|---|
| Exp 1 | 0 | 1 | 0 | 1 | 0 | 0 0 0 0 0 |  |
| Exp 2 | 0 | 0 | 0 | 2 | 0 | 0 0 0 0 0 |  |
| Exp 3 | 0 | 2 | 0 | 0 | 0 | 0 0 0 0 0 |  |

Particles tested  4.5E+11        4.5E+11
Number of RCAs      6*                0

- Statistical analysis: Study of the conditional probability of the observation.

*:The results obtained are different; p<5% - Confidence interval = 98.5%

Figure 12

SEQUENCE LISTING

<160> NUMBER OF SEQ ID NOS: 16

<210> SEQ ID NO 1
<211> LENGTH: 424
<212> TYPE: DNA
<213> ORGANISM: Artificial Sequence
<220> FEATURE:
<221> NAME/KEY: CDS
<222> LOCATION: (1)..(420)
<223> OTHER INFORMATION: Description of Artificial Sequence: Degenerate
      pIX gene

<400> SEQUENCE: 1

```
atg tcc acg aat tcc ttt gac ggc tcc atc gtc tcc agc tac ctg acc      48
Met Ser Thr Asn Ser Phe Asp Gly Ser Ile Val Ser Ser Tyr Leu Thr
 1               5                  10                  15 acc cgg atg cct ccc tgg gct ggc gtc cgc caa aac gtc atg gga agc      96
Thr Arg Met Pro Pro Trp Ala Gly Val Arg Gln Asn Val Met Gly Ser
             20                  25                  30 tcc atc gac ggc agg cct gtg ctc cct gcc aat agc acc act ctg act     144
Ser Ile Asp Gly Arg Pro Val Leu Pro Ala Asn Ser Thr Thr Leu Thr
         35                  40                  45 tat gaa act gtc agc ggc acc cca ctg gaa acc gcc gca agc gct gca     192
Tyr Glu Thr Val Ser Gly Thr Pro Leu Glu Thr Ala Ala Ser Ala Ala
     50                  55                  60 gcc agc gct gcc gcc gct act gct cgg ggc atc gtc acc gat ttc gcc     240
Ala Ser Ala Ala Ala Ala Thr Ala Arg Gly Ile Val Thr Asp Phe Ala
 65                  70                  75                  80 ttt ctc tcc cct ctg gcc tcc agc gct gcc agc cgc agc tct gct cgg     288
Phe Leu Ser Pro Leu Ala Ser Ser Ala Ala Ser Arg Ser Ser Ala Arg
                 85                  90                  95 gac gat aaa ctg acc gcc ctg ctg gct cag ctg gac agc ctg act agg     336
Asp Asp Lys Leu Thr Ala Leu Leu Ala Gln Leu Asp Ser Leu Thr Arg
            100                 105                 110 gag ctg aac gtg gtg agc caa caa ctc ctg gac ctc cgg caa caa gtg     384
Glu Leu Asn Val Val Ser Gln Gln Leu Leu Asp Leu Arg Gln Gln Val
        115                 120                 125 agc gct ctc aaa gcc tct agc cca cct aac gcc gtt taaa                424
Ser Ala Leu Lys Ala Ser Ser Pro Pro Asn Ala Val
    130                 135                 140
```

<210> SEQ ID NO 2
<211> LENGTH: 140
<212> TYPE: PRT
<213> ORGANISM: Artificial Sequence
<220> FEATURE:
<223> OTHER INFORMATION: Description of Artificial Sequence: Degenerate
      pIX gene

<400> SEQUENCE: 2

```
Met Ser Thr Asn Ser Phe Asp Gly Ser Ile Val Ser Ser Tyr Leu Thr
 1               5                  10                  15

Thr Arg Met Pro Pro Trp Ala Gly Val Arg Gln Asn Val Met Gly Ser
             20                  25                  30

Ser Ile Asp Gly Arg Pro Val Leu Pro Ala Asn Ser Thr Thr Leu Thr
         35                  40                  45

Tyr Glu Thr Val Ser Gly Thr Pro Leu Glu Thr Ala Ala Ser Ala Ala
     50                  55                  60

Ala Ser Ala Ala Ala Ala Thr Ala Arg Gly Ile Val Thr Asp Phe Ala
 65                  70                  75                  80
```

```
Phe Leu Ser Pro Leu Ala Ser Ser Ala Ala Ser Arg Ser Ser Ala Arg
             85                  90                  95

Asp Asp Lys Leu Thr Ala Leu Leu Ala Gln Leu Asp Ser Leu Thr Arg
            100                 105                 110

Glu Leu Asn Val Val Ser Gln Gln Leu Leu Asp Leu Arg Gln Gln Val
            115                 120                 125

Ser Ala Leu Lys Ala Ser Ser Pro Pro Asn Ala Val
            130                 135             140

<210> SEQ ID NO 3
<211> LENGTH: 357
<212> TYPE: DNA
<213> ORGANISM: Artificial Sequence
<220> FEATURE:
<221> NAME/KEY: CDS
<222> LOCATION: (1)..(354)
<223> OTHER INFORMATION: Description of Artificial Sequence: Degenerate
      IVa2 gene

<400> SEQUENCE: 3 atc gcg aac cta aaa ata cag tcc aag atg cat ctg ata tcc cca cgt      48
Ile Ala Asn Leu Lys Ile Gln Ser Lys Met His Leu Ile Ser Pro Arg
 1               5                  10                  15 atg cac ccc tcc cag ctt aac cgc ttc gta aac act tac acc aag gga      96
Met His Pro Ser Gln Leu Asn Arg Phe Val Asn Thr Tyr Thr Lys Gly
             20                  25                  30 ctg ccc ctg gca atc agc ctg cta ctg aaa gac att ttc agg cac cac     144
Leu Pro Leu Ala Ile Ser Leu Leu Leu Lys Asp Ile Phe Arg His His
         35                  40                  45 gcc cag cgg tcc tgc tac gac tgg att atc tac aac acc act ccg cag     192
Ala Gln Arg Ser Cys Tyr Asp Trp Ile Ile Tyr Asn Thr Thr Pro Gln
     50                  55                  60 cat gaa gct ctc cag tgg tgc tac ctc cat ccc aga gac ggg ctt atg     240
His Glu Ala Leu Gln Trp Cys Tyr Leu His Pro Arg Asp Gly Leu Met
 65                  70                  75                  80 cct atg tat ctg aac atc cag agc cac ctt tac cac gtc ctc gaa aaa     288
Pro Met Tyr Leu Asn Ile Gln Ser His Leu Tyr His Val Leu Glu Lys
                 85                  90                  95 ata cac agg acc ctg aac gac cga gac cgc tgg tct cgg gcc tac cgc     336
Ile His Arg Thr Leu Asn Asp Arg Asp Arg Trp Ser Arg Ala Tyr Arg
            100                 105                 110 gcg cgg aaa acc cct aaa taa                                         357
Ala Arg Lys Thr Pro Lys
            115

<210> SEQ ID NO 4
<211> LENGTH: 118
<212> TYPE: PRT
<213> ORGANISM: Artificial Sequence
<220> FEATURE:
<223> OTHER INFORMATION: Description of Artificial Sequence: Degenerate
      IVa2 gene

<400> SEQUENCE: 4

Ile Ala Asn Leu Lys Ile Gln Ser Lys Met His Leu Ile Ser Pro Arg
 1               5                  10                  15

Met His Pro Ser Gln Leu Asn Arg Phe Val Asn Thr Tyr Thr Lys Gly
             20                  25                  30

Leu Pro Leu Ala Ile Ser Leu Leu Leu Lys Asp Ile Phe Arg His His
         35                  40                  45

Ala Gln Arg Ser Cys Tyr Asp Trp Ile Ile Tyr Asn Thr Thr Pro Gln
     50                  55                  60
```

```
His Glu Ala Leu Gln Trp Cys Tyr Leu His Pro Arg Asp Gly Leu Met
 65                  70                  75                  80

Pro Met Tyr Leu Asn Ile Gln Ser His Leu Tyr His Val Leu Glu Lys
                 85                  90                  95

Ile His Arg Thr Leu Asn Asp Arg Asp Arg Trp Ser Arg Ala Tyr Arg
            100                 105                 110

Ala Arg Lys Thr Pro Lys
        115

<210> SEQ ID NO 5
<211> LENGTH: 941
<212> TYPE: DNA
<213> ORGANISM: Artificial Sequence
<220> FEATURE:
<223> OTHER INFORMATION: Description of Artificial Sequence: Syngen#1

<400> SEQUENCE: 5
ggccggccgt cgactgtgtg ggcgtggctt aagggtggga agaatatat  aaggtggggg      60 tcttatgtag ttttgtatct gttttgcagc agccgccgcc gccatgtcca cgaattcctt     120
tgacggctcc atcgtctcca gctacctgac cacccggatg cctccctggg ctggcgtccg     180
ccaaaacgtc atgggaagct ccatcgacgg caggcctgtg ctccctgcca atagcaccac     240
tctgacttat gaaactgtca gcggcacccc actggaaacc gccgcaagcg ctgcagccag     300
cgctgccgcc gctactgctc ggggcatcgt caccgatttc gcctttctct cccctctggc     360
ctccagcgct gccagccgca gctctgctcg ggacgataaa ctgaccgccc tgctggctca     420
gctggacagc ctgactaggg agctgaacgt ggtgagccaa caactcctgg acctccggca     480
acaagtgagc gctctcaaag cctctagccc acctaacgcc gtttaaaaca taaataaaaa     540
accagactct gtttggattt ggatcaagca agtgtcttgc tgtctttatt taggagtttt     600
ccgcgcgcgg taggcccgag accagcggtc tcggtcgttc agggtcctgt gtattttttc     660
gaggacgtgg taaaggtggc tctggatgtt cagatacata ggcataagcc cgtctctggg     720
atggaggtag caccactgga gagcttcatg ctgcggagtg gtgttgtaga taatccagtc     780
gtagcaggac cgctgggcgt ggtgcctgaa aatgtctttc agtagcaggc tgattgccag     840
gggcagtccc ttggtgtaag tgtttacgaa gcggttaagc tgggaggggt gcatacgtgg     900
ggatatgaga tgcatcttgg actgtatttt taggttcgcg a                        941

<210> SEQ ID NO 6
<211> LENGTH: 423
<212> TYPE: DNA
<213> ORGANISM: Artificial Sequence
<220> FEATURE:
<221> NAME/KEY: CDS
<222> LOCATION: (1)..(423)
<223> OTHER INFORMATION: Description of Artificial Sequence: Degenerate
      pIX gene

<400> SEQUENCE: 6 atg agc acg aat tcg ttt gac gga agc atc gtc agc tca tac ttg acc       48
Met Ser Thr Asn Ser Phe Asp Gly Ser Ile Val Ser Ser Tyr Leu Thr
 1               5                  10                  15 acg cgc atg cct ccc tgg gcc ggg gtg cgc cag aat gtc atg ggc tcc       96
Thr Arg Met Pro Pro Trp Ala Gly Val Arg Gln Asn Val Met Gly Ser
            20                  25                  30 agc att gac ggt cgc cct gtc ctg cct gca aac tct acc act ttg acc      144
Ser Ile Asp Gly Arg Pro Val Leu Pro Ala Asn Ser Thr Thr Leu Thr
        35                  40                  45
```

-continued

```
tac gaa acc gtg tct ggc acg ccg ttg gaa act gca gca tcc gcc gcc      192
Tyr Glu Thr Val Ser Gly Thr Pro Leu Glu Thr Ala Ala Ser Ala Ala
 50                  55                  60 gct agc gcc gct gca gct acc gcc cgc ggg atc gtg act gat ttt gct      240
Ala Ser Ala Ala Ala Ala Thr Ala Arg Gly Ile Val Thr Asp Phe Ala
 65                  70                  75                  80 ttt ctg agc ccg ctt gcc agc agt gca gcc tcc cgt tca tct gcc cgc      288
Phe Leu Ser Pro Leu Ala Ser Ser Ala Ala Ser Arg Ser Ser Ala Arg
                 85                  90                  95 gat gac aaa ttg acg gct ctt ctg gct cag ctg gat tct ttg act cgg      336
Asp Asp Lys Leu Thr Ala Leu Leu Ala Gln Leu Asp Ser Leu Thr Arg
            100                 105                 110 gaa ctt aac gtc gtt tct cag caa ctg ttg gac ctg cgc cag caa gtt      384
Glu Leu Asn Val Val Ser Gln Gln Leu Leu Asp Leu Arg Gln Gln Val
        115                 120                 125 tct gcc ctc aag gct tct tcc cct ccc aat gcc gtt taa                  423
Ser Ala Leu Lys Ala Ser Ser Pro Pro Asn Ala Val
    130                 135                 140
```

<210> SEQ ID NO 7
<211> LENGTH: 140
<212> TYPE: PRT
<213> ORGANISM: Artificial Sequence
<220> FEATURE:
<223> OTHER INFORMATION: Description of Artificial Sequence: Degenerate
      pIX gene

<400> SEQUENCE: 7

```
Met Ser Thr Asn Ser Phe Asp Gly Ser Ile Val Ser Ser Tyr Leu Thr
 1               5                  10                  15

Thr Arg Met Pro Pro Trp Ala Gly Val Arg Gln Asn Val Met Gly Ser
             20                  25                  30

Ser Ile Asp Gly Arg Pro Val Leu Pro Ala Asn Ser Thr Thr Leu Thr
         35                  40                  45

Tyr Glu Thr Val Ser Gly Thr Pro Leu Glu Thr Ala Ala Ser Ala Ala
 50                  55                  60

Ala Ser Ala Ala Ala Ala Thr Ala Arg Gly Ile Val Thr Asp Phe Ala
 65                  70                  75                  80

Phe Leu Ser Pro Leu Ala Ser Ser Ala Ala Ser Arg Ser Ser Ala Arg
                 85                  90                  95

Asp Asp Lys Leu Thr Ala Leu Leu Ala Gln Leu Asp Ser Leu Thr Arg
            100                 105                 110

Glu Leu Asn Val Val Ser Gln Gln Leu Leu Asp Leu Arg Gln Gln Val
        115                 120                 125

Ser Ala Leu Lys Ala Ser Ser Pro Pro Asn Ala Val
    130                 135                 140
```

<210> SEQ ID NO 8
<211> LENGTH: 270
<212> TYPE: DNA
<213> ORGANISM: Artificial Sequence
<220> FEATURE:
<221> NAME/KEY: CDS
<222> LOCATION: (1)..(270)
<223> OTHER INFORMATION: Description of Artificial Sequence: Degenerate
      IVa2 gene

<400> SEQUENCE: 8

```
acc aag ggc ctg ccc ctc gca atc agc ttg cta ctc aaa gac att ttt       48
Thr Lys Gly Leu Pro Leu Ala Ile Ser Leu Leu Leu Lys Asp Ile Phe
 1               5                  10                  15
```

```
agg cat cac gcc cag cgc tcc tgt tac gac tgg atc atc tac aat acc    96
Arg His His Ala Gln Arg Ser Cys Tyr Asp Trp Ile Ile Tyr Asn Thr
            20                  25                  30 acc ccg cag cat gaa gcc ctg cag tgg tgc tac ctg cac ccc aga gac   144
Thr Pro Gln His Glu Ala Leu Gln Trp Cys Tyr Leu His Pro Arg Asp
        35                  40                  45 ggg ctg atg ccc atg tat ctg aat atc cag agt cac ctt tat cac gtc   192
Gly Leu Met Pro Met Tyr Leu Asn Ile Gln Ser His Leu Tyr His Val
    50                  55                  60 ctg gaa aaa ata cat agg acc ctc aac gac cga gat cgc tgg tcc cgg   240
Leu Glu Lys Ile His Arg Thr Leu Asn Asp Arg Asp Arg Trp Ser Arg
65                  70                  75                  80 gcc tat cgc gcg cgc aaa acc cct aaa taa                           270
Ala Tyr Arg Ala Arg Lys Thr Pro Lys
                85                  90

<210> SEQ ID NO 9
<211> LENGTH: 89
<212> TYPE: PRT
<213> ORGANISM: Artificial Sequence
<220> FEATURE:
<223> OTHER INFORMATION: Description of Artificial Sequence: Degenerate
      IVa2 gene

<400> SEQUENCE: 9

Thr Lys Gly Leu Pro Leu Ala Ile Ser Leu Leu Leu Lys Asp Ile Phe
 1               5                  10                  15

Arg His His Ala Gln Arg Ser Cys Tyr Asp Trp Ile Ile Tyr Asn Thr
            20                  25                  30

Thr Pro Gln His Glu Ala Leu Gln Trp Cys Tyr Leu His Pro Arg Asp
        35                  40                  45

Gly Leu Met Pro Met Tyr Leu Asn Ile Gln Ser His Leu Tyr His Val
    50                  55                  60

Leu Glu Lys Ile His Arg Thr Leu Asn Asp Arg Asp Arg Trp Ser Arg
65                  70                  75                  80

Ala Tyr Arg Ala Arg Lys Thr Pro Lys
                85

<210> SEQ ID NO 10
<211> LENGTH: 103
<212> TYPE: DNA
<213> ORGANISM: Artificial Sequence
<220> FEATURE:
<223> OTHER INFORMATION: Description of Artificial Sequence: pIX
      modified promoter

<400> SEQUENCE: 10
ggccggccgt cgactgtgtg ggcgtggcat aagggtggga agaatatat aaggtcgggg    60 tctcatctag tcttgtatct gatttgcagt agccgccgcc acc                    103

<210> SEQ ID NO 11
<211> LENGTH: 52
<212> TYPE: DNA
<213> ORGANISM: Adenovirus
<220> FEATURE:
<223> OTHER INFORMATION: Polyadenylation region

<400> SEQUENCE: 11
agatctcaaa tcaataaata aagaaatact tgttataaaa acaaatgaat gt           52

<210> SEQ ID NO 12
```

```
<211> LENGTH: 847
<212> TYPE: DNA
<213> ORGANISM: Artificial Sequence
<220> FEATURE:
<223> OTHER INFORMATION: Description of Artificial Sequence: Syngen #2

<400> SEQUENCE: 12
ggccggccgt cgactgtgtg ggcgtggcat aagggtggga agaatatat aaggtcgggg      60 tctcatctag tcttgtatct gatttgcagt agccgccgcc accatgagca cgaattcgtt     120
tgacggaagc atcgtcagct catacttgac cacgcgcatg cctccctggg ccggggtgcg     180
ccagaatgtc atgggctcca gcattgacgg tcgccctgtc ctgcctgcaa actctaccac     240
tttgacctac gaaaccgtgt ctggcacgcc gttggaaact gcagcatccg ccgccgctag     300
cgccgctgca gctaccgccc gcgggatcgt gactgatttt gcttttctga gcccgcttgc     360
cagcagtgca gcctcccgtt catctgcccg cgatgacaaa ttgacggctc ttctggctca     420
gctggattct ttgactcggg aacttaacgt cgtttctcag caactgttgg acctgcgcca     480
gcaagtttct gccctcaagg cttcttcccc tcccaatgcc gtttaaagat ctcaaatcaa     540
taaataaaga aatacttgtt ataaaaacaa atgaatgttt atttaggggt tttgcgcgcg     600
cgataggccc gggaccagcg atctcggtcg ttgagggtcc tatgtatttt ttccaggacg     660
tgataaaggt gactctggat attcagatac atgggcatca gcccgtctct ggggtgcagg     720
tagcaccact gcagggcttc atgctgcggg gtggtattgt agatgatcca gtcgtaacag     780
gagcgctggg cgtgatgcct aaaaatgtct ttgagtagca agctgattgc gaggggcagg     840
cccttgg                                                               847

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: PCR Primer

<400> SEQUENCE: 13
aactgcaggc cggccactag tcgcgatgtt cccagccata tccc                       44

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: PCR Primer

<400> SEQUENCE: 14
ccgctcgagg tgaccgctag ccattatgga cgaatgc                               37

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: PCR Primer

<400> SEQUENCE: 15
atcgatcgat aacagtcagc cttacc                                           26

<210> SEQ ID NO 16
<211> LENGTH: 28
<212> TYPE: DNA
<213> ORGANISM: Artificial Sequence
```

-continued

```
<220> FEATURE:
<223> OTHER INFORMATION: Description of Artificial Sequence: PCR Primer

<400> SEQUENCE: 16
agctgaattc catcatcaat aatatacc                                              28
```

ADENOVIRUS VECTORS AND METHOD FOR REDUCING HOMOLOGOUS RECOMBINATION PHENOMENA

The present invention relates to a method for reducing recombination events between nucleic acids. It also relates to the use of this method in processes for preparing nucleic acids such as plasmids or viral vectors. The invention also relates to novel viral constructs.

Recombination between nucleic acids is a well known phenomenon of molecular biology. Recombination is a molecular mechanism by which novel combinations of genetic material are generated, which contribute to Darwinian evolution by providing a source of material for natural selection. Genetic recombination requiring strong sequence homology between the participating nucleic acids is generally referred to as homologous recombination. During homologous recombination events, an exchange of genetic information occurs between two regions of a nucleic acid, this exchange possibly being reciprocal ("crossing over") or nonreciprocal (conversion).

During meiosis, homologous recombination is responsible for the rearrangement of the genetic information and plays an important role in the correct segregation of the chromosomes. During mitosis, homologous recombination participates in DNA repair. It can introduce genomic rearrangements, such as deletions and duplications, when it involves dispersed homologous regions, or also contractions or expansions when it involves tandem repeat sequences.

The mechanism by which homologous recombination occurs has been partly elucidated. Thus, in bacteria, homologous recombination begins with a step which involves a single-stranded end (Holliday, 1964; Meselson, 1975). In eukaryotes, on the other hand, most results suggest a mechanism of double-strand break (DSB) (Szostak et al., 1983). DSBs appear to be at the origin of two principal mechanisms of homologous recombination: one conservative, according to which all the nucleic acid sequences participating in the recombination are present in the recombination products (Szostak et al.), the other nonconservative, during which certain sequences are lost. In mammalian somatic cells the majority of homologous recombination events by DSB appear to take place according to a nonconservative process (Lin et al., 1990, Jeong-Yu, 1992).

With the constant-development of biotechnology, an ever-increasing exploitation of DNA is being carried out: production of recombinant proteins, creation of transgenic animals, gene therapy and cellular therapy, etc. In these different domains, the occurrence of uncontrolled recombination events can constitute, in certain cases, a drawback.

Thus, during the production of recombinant proteins, recombination events in the expression plasmid (intramolecular recombination) can for example lead to the excision of the expression cassette for the transgene and thus to a loss of the expression. Recombination events can also be at the origin of the excision of an expression cassette which is stably integrated into the genome of a host producer cell and thus can induce a loss of stability.

Another example of adverse effects linked to the occurrence of homologous recombination events is liable to take place during the construction and production of vectors, in particular of viral vectors. Viral vectors (adenovirus, retrovirus, adeno-associated virus, herpes virus, etc.) constitute particularly efficient means for transferring nucleic acids into cells in vitro, ex vivo or in vivo. For constructing defective viral vectors the regions which are essential for the replication of the wild-type virus are generally deleted from the genome and replaced with the nucleic acid of interest. To produce and amplify these viruses it is therefore necessary to supply, in trans, the complementing functions (either in a plasmid, or in a form which is integrated into the genome of the producer cell, or via a helper virus). However, in certain cases, homologous recombination events occur between the defective viral genome and the complementing functions, which reconstitute replicating viral particles. Thus, the vectors derived from adenoviruses are generally produced in a complementing line (293 line or derivative) into which part of the adenovirus genome has been integrated. More specifically, the 293 line contains the left-hand end (about 11–12%) of the genome of the adenovirus serotype 5 (Ad5), comprising the left ITR, the encapsidation region and the E1 region, including E1a, E1b, and part of the regions encoding the protein pIX and IVa2. This line is capable of transcomplementing recombinant adenoviruses which are defective for the E1 region, i.e. lacking in all or part of the E1 region, which is required for replication. However, there exist zones of homology between the region of the adenovirus which is integrated into the genome of the line and the DNA of the recombinant virus whose production is desired. For this reason, various recombination events can take place during production, generating replicating viral particles, in particular adenoviruses of type E1+. As indicated in FIG. 1, it can be a single recombination event followed by a break of the chromosome (FIG. 1A), or a double recombination (FIG. 1B). These two types of modification lead to the replacement of the left-hand portion of the recombinant DNA, lacking in a functional E1 region, with the corresponding portion present in the cell's genome, which carries a functional copy of the E1 region. Moreover, taking into account the high titres of recombinant vector produced by the 293 line, the probability of these recombination events taking place is high. In fact, it has been found that many batches of defective recombinant adenoviral vectors are contaminated with replicating viral particles.

The presence of replicating particles in the batches of virus constitutes a considerable drawback for applications for transferring genes in vitro or in vivo (risks of viral propagation and uncontrolled dissemination).

The same type of problematics exist for generating defective retroviruses. Thus, constructed defective retroviruses are generally deleted of the viral coding regions (gag, pol and env), which are provided in trans by the production line. Here again, for certain lines described, overlapping zones exist between the genome of the defective retrovirus and the complementing functions carried by the cells. It is the case in particular for the cells PA317, Psi2, etc. Homologous recombination events can therefore take place in these zones, generating replicating particles.

The present invention relates to a method for reducing the frequency of the recombination events between two given nucleic acids and thus for minimizing the impact of such events on a biological process.

More particularly, the present invention relates to a method for reducing the frequency of the homologous recombination events between two given nucleic acids or two regions of a nucleic acid. To reduce homologous recombination events, the prior art teaches various approaches which are all based on the same principle: replacing or deleting the regions of homology. Thus, certain plasmids which allow the expression of genes of interest carry regions which are homologous to the genome of the host cell. It can be, in particular, a promoter region, a marker gene or an origin of replication. To reduce the risks of recombination, it has hitherto been proposed to substitute these regions with others, which are nonhomologous (different promoter, etc.). Moreover, to limit the risks of recombination in the processes for producing viral vectors, it has been suggested to remove the sequences which are homologous between the complementing genes and the defective viral genome. Thus, patent application WO 97/00326 describes a cell line for producing adenovirus, designated PER, comprising a restricted unit of the adenoviral genome carrying the E1 region. With this line, the flanking sequences which are homologous to the genome of the defective virus are reduced, which makes it possible to limit the risks of homologous recombination between them. Similarly, application WO 95/11984 describes the construction of a recombinant adenovirus carrying a deletion of the E1 region which is extended to a portion of the pIX gene. In this case, it is no longer the complementing region which is modified (reduced), but the deletion carried in the defective genome, which is extended. The result is also a decrease in the risks of recombination, even if regions of homology remain.

However, while these approaches make it possible to reduce the risks of recombination between the cell and the viral genome, and thus the risks of producing batches of virus which are contaminated with replicating particles, they do not make it possible to eliminate them entirely, and/or require the as construction and thus the validation of novel cell lines, which is very laborious. Moreover, the substitution of regions with others is not necessarily satisfactory, in particular in terms of efficacy.

The present application describes a novel method for reducing inter- or intramolecular homologous recombination events. The invention also describes the application of this method to the production of defective viruses which are not contaminated with replicating particles. The invention also describes novel viral constructs, which can be amplified in the existing production lines which are the most efficient in terms of the titre, with greatly reduced risks of generating replicating particles.

The initial and important step of homologous recombination is the recognition between the two partner nucleic acids (intermolecular recombination) or between two regions of a nucleic acid (intramolecular recombination). This step is the result of a direct interaction between the two homologous regions. Homologous recombination between two nucleic acids is thus based on the existence of sequence identity or strong sequence homology between two regions of these nucleic acids and is generally dependent upon two factors: the degree of homology and the length of the homology (i.e. of the homologous regions carried by the nucleic acid or the two nucleic acids). Moreover, the frequency of homologous recombination can also be influenced by certain specific regions of the nucleic acids. Thus, it has been observed that certain regions are capable of recombining with a frequency which is higher than the average frequency. It has moreover been determined that these localized variations in frequency could be due to specific sequences such as CHI sites in *E. coli* or M26 sites in *S. pombe* (Gangloff et al., 1994).

Unlike the strategies proposed in the prior art, the method of the invention does not involve deletion of the zones of homology between the partner nucleic acids. The method of the invention is based, in an original way, on the modification of the sequence of at least one of the two partner nucleic acids of the recombination, in such a way as to reduce the homology which exists between these nucleic acids.

A first subject of the invention thus relates to a method for reducing the frequency of intra- or intermolecular homologous recombination events between nucleic acids, characterized in that the sequence of at least one of the partner nucleic acids of the recombination is degenerated in such a way as to reduce the homology with the other partner(s).

For the purposes of the invention, "reduction of the frequency of homologous recombination events" between nucleic acids is taken to mean any lowering of the said frequency, relative to the frequency observed with the unmodified corresponding nucleic acids. This reduction can easily be measured by conventional tests known to persons skilled in the art (in particular by "marker rescue" tests or by tests for generation of replicating viral particles). Advantageously, the term "reduction" is understood as a significant drop in the frequency of homologous recombination, preferably of at least one logarithmic unit.

"Intermolecular homologous recombination" is intended to mean a homologous recombination between two different nucleic acids (or between two regions of two different nucleic acids). "Intramolecular homologous recombination" is intended to mean a homologous recombination between two regions of the same nucleic acid. Moreover, the partner nucleic acids of the homologous recombination can be extrachromosomal nucleic acids, chromosomal nucleic acids or a combination of the two (i.e. a chromosomal nucleic acid and an extrachromosomal nucleic acid). The extrachromosomal nucleic acids can be plasmids, vectors, episomes, viral genomes, etc.

The method of the invention is particularly suited to reducing the frequency of the intermolecular homologous recombination events between a chromosomal nucleic acid and an extrachromosomal nucleic acid.

The method of the invention generally involves the following steps:

(i) identification of the region(s) responsible for the homologous recombination (ii) modification of this or these regions (iii) verification of the sequence (iv) synthesis of the modified sequence (referred to as syngen)

(v) replacement of the original sequence with the syngen (i) The identification of the regions responsible for homologous recombination between nucleic acids is carried out by any known method. In particular, as soon as a recombination event is observed, the regions which are responsible therefor can be investigated by sequence analysis: investigation of homologous regions between the nucleic acids (intermolecular) or within the nucleic acid (intramolecular).

When the sequences involved in the recombination are identified, a region is defined, comprising all or part of these sequences, which is used for step (ii) below, i.e. the modification.

(ii) Modification of the Sequence

It is generally accepted that the homology must be very strong over a sufficiently long region for recombination event to take place at a significant frequency. In particular, the data from the literature suggest that a region of perfect homology at least equal to about 200 pb in length is required for the occurrence of such events. Indeed, even though recombination events can take place over shorter regions, their frequency is much lower and irregular. Moreover, over such a region whose homology is reduced by 19%, it appears that the frequency of recombination is reduced by a factor 1000 (Waldman and Liskay, 1987).

The sequence can be modified in various ways. As regards coding sequence, modifications can be introduced based on the degeneracy of the genetic code. In this way the sequence is disturbed, and thus the homology is reduced, but the expression product is the same.

The invention resides therefore, in particular, in a modification of the sequence in such a way as to prevent the pairing between the two homologous regions. The modification makes it possible to decrease the length and degree of homology between the two regions concerned.

Advantageously, in the method of the invention, the sequence of the nucleic acid is degenerated, in the region involved in the homologous recombination, in a proportion of 1 base pair at least every 20 base pairs. More preferably, it is degenerated in a proportion of 1 base pair at least every 10 base pairs.

According to one particular variant of the invention, the sequence is degenerated over all the possible positions.

The degeneracy of the sequence according to the invention is advantageously produced as a function of the codon use of the cell or organism in which the nucleic acid should be used. In the case of a viral vector whose production is carried out in a human cell line, it is particularly advantageous to degenerate the sequences by favouring the preferred codon use in humans when this choice is possible (see examples).

Moreover, further modifications can be introduced into the nucleic acid sequence. Thus, in the noncoding regions it is possible to reduce the size of certain elements (regulatory sequences for expression, promoters) or to modify these elements or to substitute certain other elements with heterologous regions.

According to one particular variant of the invention, and when the zone of homology stretches over several genes, it is possible to reduce the zone of homology, on the one hand by degenerating the sequence of one or more genes, and on the other hand by modifying the genomic position of certain genes present in the zone of homology, i.e. by positioning these genes in the adenoviral genome and in a genomic position other than their original position. The sequence of the genes whose genomic position is modified can also be degenerated. Preferably, only the sequence of the genes which are not moved is degenerated.

(iii) Verification of the Sequence

The verification is carried out by data-processing methods which make it possible to detect the presence of regulatory elements, secondary structures, etc., which are liable to interfere with the activity of the syngen. See examples.

(iv) Synthesis of the Syngen

The syngen can be synthesized by any technique known to persons skilled in the art, and particularly by using nucleic acid synthesizers.

(v) Replacement of the Original Sequence With the Syngen

The syngen, once synthesized, is then introduced into the nucleic acid as a replacement for the original sequence. This step can also be carried out according to conventional molecular biology techniques well known to persons skilled in the art.

One of the applications of the method of the invention resides in the production of vectors, in particular viral vectors, devoid of replication-competent viral particles (RCV). In this respect, the method of the invention is directed more particularly towards reducing the frequency of the homologous recombination events between a chromosomal nucleic acid encoding complementing functions for a defective virus, and an extrachromosomal nucleic acid comprising the genome of the said defective virus.

The virus concerned can be advantageously an adenovirus, a retrovirus, an adeno-associated virus (AAV) or alternatively a herpes virus. It is more preferably an adenovirus.

Thus, one particular embodiment of the invention consists of a method for reducing the frequency of the homologous recombination events between a chromosomal nucleic acid comprising the E1 region of an adenovirus genome, as well as a flanking region, and an extrachromosomal nucleic acid comprising a genome of an adenovirus which is defective for the E1 region.

Advantageously, in this particular method, the degenerate sequence according to the invention comprises the pIX gene of the genome of the adenovirus which is defective for the E1 region. Even more preferably, the degenerate sequence comprises the pIX and IVa2 genes of the genome of the adenovirus.

According to another embodiment, the degenerate sequence comprises the pIX gene of the genome of the adenovirus, and the sequence of the Iva2 gene is moved from its natural locus to the E4 region.

The method of the invention is particularly suited to producing recombinant adenoviruses which are defective for the E1 region, in the 293 cell line or in a derived cell line.

As indicated above, the 293 cell line contains in its genome the left-hand portion of the genome of the adenovirus comprising in particular the E1 region and a flanking region which is located downstream (3') of the E1 region and which carries in particular the pIX gene and part of the IVa2 gene. It is precisely in this flanking region that homologous recombination events which generate replication-competent adenoviruses (RCAs) take place. For the purposes of the invention, "derived cell line" is intended to mean a cell line carrying the E1 region of the adenovirus and a flanking region liable to give rise to recombination with the defective virus. It can be a shorter region than that present in 293 (limited to pIX for example) or a longer region. A derived line can also be a line which is constructed from 293-line cells by introducing additional complementing sequences (such as E4).

In this respect, the invention also relates to a method for preparing defective recombinant adenovirus by introducing, into a cell of the 293 line or into a derived cell, the genome of the said defective recombinant adenovirus, characterized in that the said genome carries:

a deletion of the E1 region a degeneracy in the pIX and/or IVa2 genes.

The invention in addition relates to any viral vector whose genome comprises at least one region whose sequence is degenerated. It can be in particular retroviruses (carrying degenerate sequences in the gag, pol and/or env genes), AAVs (carrying degenerate sequences in the rep and/or cap genes) or also adenoviruses.

It is advantageously adenoviruses whose genome carries a degenerate pIX gene. Preferably, the degenerate sequence of the pIX gene is the sequence SEQ ID NO:1 or the sequence SEQ ID NO:6. More preferably, the adenovirus in addition carries a modification of the genomic position of the Iva2 gene. This gene is advantageously positioned in the E4 region.

According to another embodiment, it is an adenovirus whose pIX and IVa2 genes are degenerate. Preferably, the natural sequence of the pIX gene is replaced with the sequence SEQ ID NO:1 or the sequence SEQ ID NO:6 and the degenerate sequence of the IVa2 gene is the sequence SEQ ID NO:2 or the sequence SEQ ID NO:8. Preferably, the natural sequence of the pIX and IVa2 genes is replaced with the sequence SEQ ID NO:5.

According to another embodiment, it is an adenovirus whose pIX and IVa2 genes are degenerate and which in addition comprises modifications of the promoter sequence of the pIX gene and/or replacement of the polyadenylation sequence of these genes. Preferably, it is an adenovirus comprising the sequence SEQ ID NO:12.

The adenovirus in addition carries advantageously at least one deletion of the E1 region. More preferably, the adenoviruses are defective for all or part of the E1 and E3 regions at least. It can also be recombinant adenoviruses which are partially or totally defective for the E1 and E4 regions, and optionally for the E3 region. Moreover, this adenovirus can be of various serotypes. As far as the adenoviruses of human origin are concerned, mention may be made preferably of those classified in group C.

Even more preferably, among the various serotypes of human adenovirus, in the context of the present invention the adenoviruses of type 2 or 5 (Ad 2 or Ad 5) are preferred. Among the various adenoviruses of animal origin, in the context of the invention adenoviruses of canine origin are preferably used, and in particular all the strains of the CAV2 adenoviruses [Manhattan strain or A26/61 strain (ATCC VR-800) for example]. Other adenoviruses of animal origin are cited in particular in application WO 94/26914 incorporated herein by way of reference. The strategies for constructing adenoviruses, as well as the sites which can be used for introducing genes of interest into these vectors are described in detail in the prior art, and in particular WO 95/02697, WO 96/10088, WO 96/13596 or WO 96/22378.

According to one particularly advantageous embodiment, in the recombinant adenoviruses of the present invention the E1 region is inactivated by deletion of a PvuII-BglII fragment running from nucleotide 454 to nucleotide 3328 in the sequence of the Ad5 adenovirus. This sequence can be accessed in the literature and also on database (see in particular Genebank No. M73260). In another preferred embodiment, the E1 region is inactivated by deletion of a HinfII-Sau3A fragment running from nucleotide 382 to nucleotide 3446.

Advantageously, the recombinant adenoviruses of the invention in addition comprise a heterologous sequence of nucleic acids whose transfer and/or expression in a cell, an organ or an organism is desired.

In particular, the heterologous DNA sequence can comprise one or more therapeutic genes and/or one or more genes encoding antigenic peptides.

The therapeutic genes which can thus be transferred are any gene whose transcription and possibly translation in the target cell generate products having a therapeutic effect.

They can be, in particular, genes encoding protein products having a therapeutic effect. The protein product thus encoded can be a protein, a peptide, an amino acid, etc. This protein product can be homologous with respect to the target cell (i.e. a product which is normally expressed in the target cell when this cell has no pathological condition). In this case, the expression of a protein makes it possible for example to offset an insufficient expression in the cell or the expression of a protein which is inactive or weakly active because of a modification, or alternatively to overexpress the said protein. The therapeutic gene can also encode a mutant of a cellular protein, which has increased stability, modified activity, etc. The protein product can also be heterologous with respect to the target cell. In this case, an expressed protein can for example complement or provide an activity which is deficient in the cell, allowing it to combat a pathological condition.

Among the therapeutic products for the purposes of the invention, mention may be made more particularly of enzymes, blood derivatives, hormones, lymphokines: interleukins, interferons, TNFs, etc. (FR 9203120), growth factors, neurotransmitters or precursors thereof or synthesis enzymes, trophic factors: BDNF, CNTF, NGF, IGF, GMF, VEGF, aFGF, bFGF, NT3, NT5, etc.; apolipoproteins: ApoAI, ApoAIV, ApoE, etc. (FR 93 05125), dystrophin or a minidystrophin (FR 9111947), tumour suppresser genes; p53, Rb, Rap1A, DCC, k-rev, etc. (FR 93 04745), the genes encoding factors which are involved in clotting; Factors VII, VIII, IX, etc., the gene encoding the protein GAX, suicide genes: thymidine kinase, cytosine deaminase, etc., genes encoding single-chain (scFv) antibodies.

The therapeutic gene can also be a gene or an antisense sequence, whose expression in the target cell makes it possible to control the expression of genes or the transcription of cellular mRNAs. Such sequences can, for example, be transcribed in the target cell into RNAs which are complementary for cellular mRNAs, and can thus block their translation into protein, according to the technique described in patent EP 140 308.

As indicated above, the heterologous DNA sequence can also comprise one or more genes encoding an antigenic peptide which is capable of generating an immune response in humans. In this particular embodiment, the invention thus allows the production of vaccines which make it possible to immunize humans, in particular against microorganisms or viruses. They can be in particular antigenic peptides specific for the Epstein-Barr virus, the HIV virus, the hepatitis B virus (EP 185 573), the pseudo-rabies virus, or alternatively specific for tumours (EP 259 212).

Generally, the heterologous nucleic acid sequence also comprises a promoter region for functional transcription in the infected cell. It can be a promoter region which is responsible naturally for the expression of the gene under consideration when this region is capable of functioning in the infected cell. It can also be regions of different origin (which are responsible for the expression of other proteins, or are even synthetic). In particular, it can be promoter sequences of eukaryotic or viral genes. For example, it can be promoter sequences derived from the genome of the cell whose infection is desired. Similarly, it can be promoter sequences derived from the genome of a virus, including the adenovirus used. In this respect, mention may be made for example of the promoters of the E1A, MLP, CMV, RSV, etc. genes. In addition, these promoter regions can be modified by addition of sequences for activation or regulation, or which allow tissue-specific or tissue-predominant expression. Moreover, when the heterologous nucleic acid does not comprise promoter sequences, it can be inserted into the genome of the defective virus downstream of such a sequence.

Moreover, the heterologous nucleic acid sequence can also comprise, in particular upstream of the therapeutic gene, a signal sequence which directs the synthesized therapeutic product in the secretory pathways of the target cell. This signal sequence can be the natural signal sequence of the therapeutic product, but it can also be any other functional signal sequence or an artificial signal sequence.

Still in a particularly advantageous embodiment, the vectors of the invention in addition possess a functional E3 gene under the control of a heterologous promoter. More preferably, the vectors possess a portion of the E3 gene which allows the expression of the protein gp19K. This protein in fact makes it possible to avoid the adenovirus vector being the object of an immune reaction which (i) would limit its action and (ii) might have adverse side effects.

These recombinant vectors can be used for transferring nucleic acids into cells in vitro, ex vivo or in vivo.

The present invention also relates to any pharmaceutical composition comprising one or more recombinant adenovirus as described above. The pharmaceutical compositions of the invention can be formulated with a view to administration by topical, oral, parental, intranasal, intravenous, intramuscular, subcutaneous, intraocular, transdermal, etc. route.

Preferably, the pharmaceutical composition contains pharmaceutically acceptable vehicles for an injectable formulation. It can be in particular isotonic, sterile saline solutions (monosodium phosphate, disodium phosphate, sodium chloride, potassium chloride, calcium chloride or magnesium chloride, etc., or mixtures of such salts) or dry compositions, in particular lyophilized compositions, which by addition of sterilized water or physiological saline, depending on the case in question, allow injectable solutions to be made up.

The doses of virus used for the injection can be adapted as a function of various parameters, and in particular as a function of the method of administration used, the pathology concerned, the gene to be expressed, or alternatively the desired duration of the treatment. Generally, the recombinant adenoviruses according to the invention are formulated and administered in the form of doses between 104 and $10^{14}$ pfu/ml, and preferably $10^6$ to $10^{10}$ pfu/ml. The term pfu ("plaque-forming unit") corresponds to the infectious power of a viral solution, and is determined by infecting an appropriate cell culture and measuring, generally after 5 days, the number of plaques of infected cells. The techniques for determining the pfu titre of a viral solution are well documented in the literature.

The present invention will be described in greater detail with the aid of the following examples, which should be considered as illustrative and non-limiting.

LEGEND TO FIGURES

FIG. 1: Recombination events between the adenovirus and the 293 line

FIG. 2: Schematic Structure of the syngen

Figure 3:
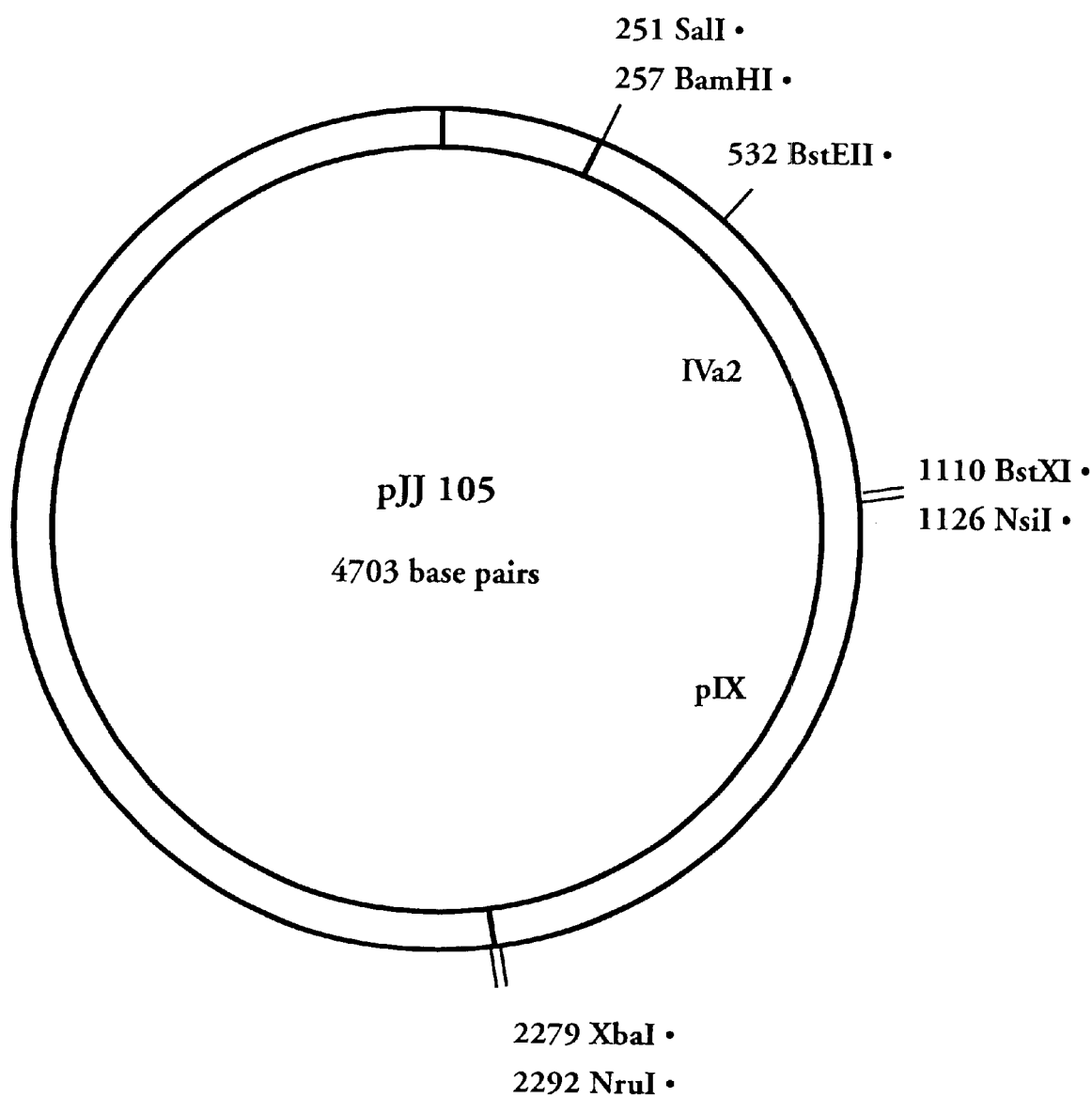

FIG. 3: Restriction map of the plasmid pJJ 105

Figure 4:
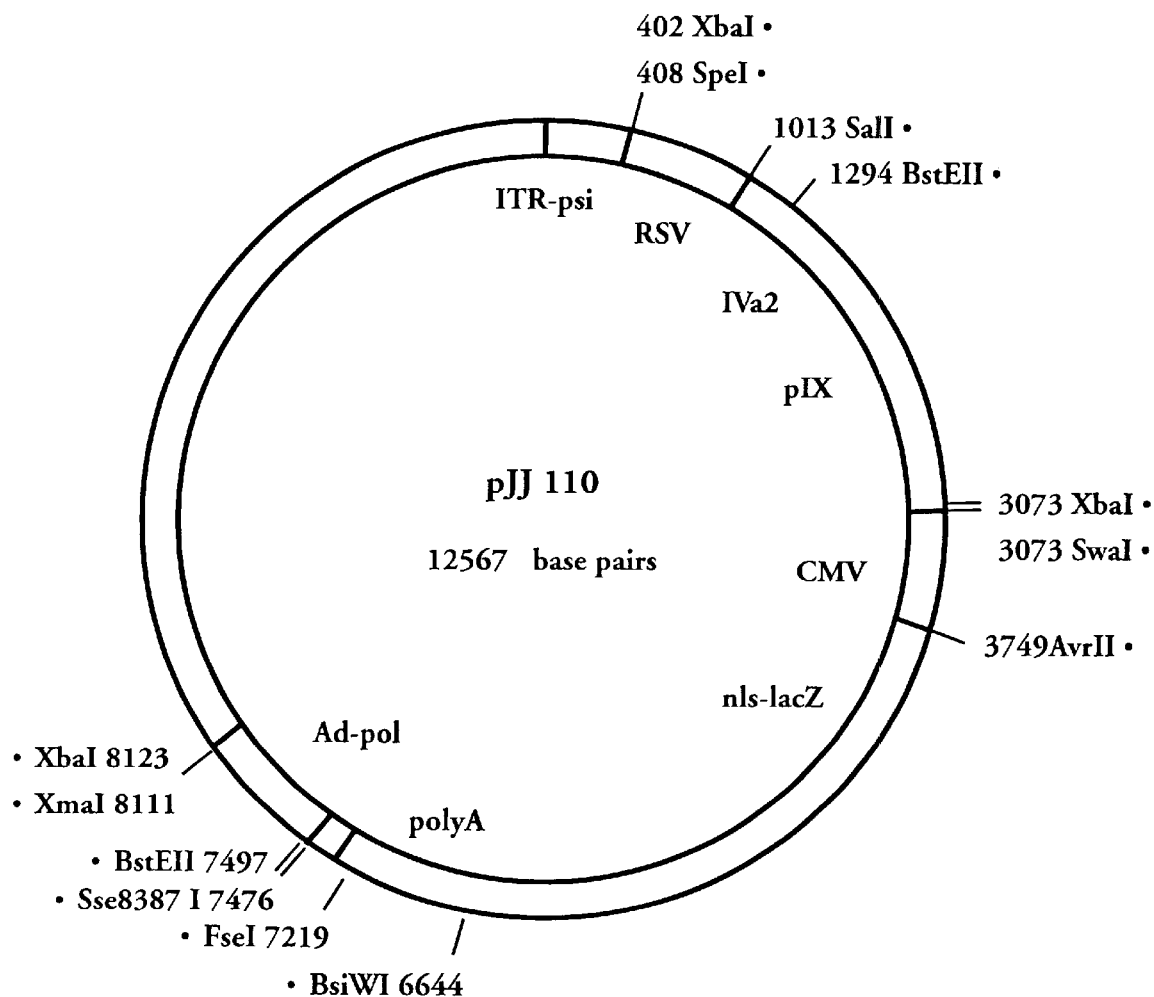

FIG. 4: Restriction map of the plasmid pJJ 110

Figure 5:
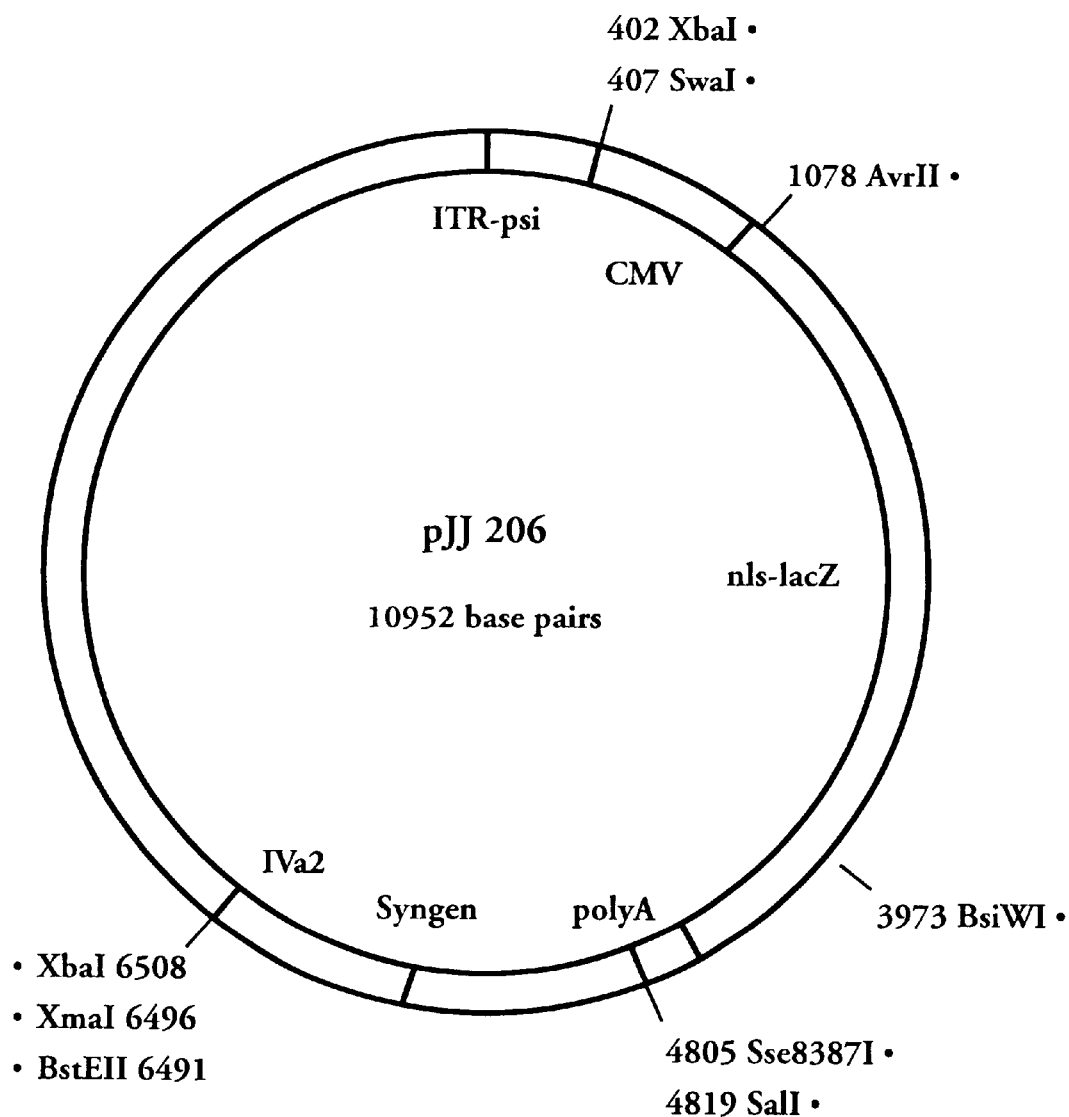

FIG. 5: Restriction map of the plasmid pJJ 206

Figure 6:
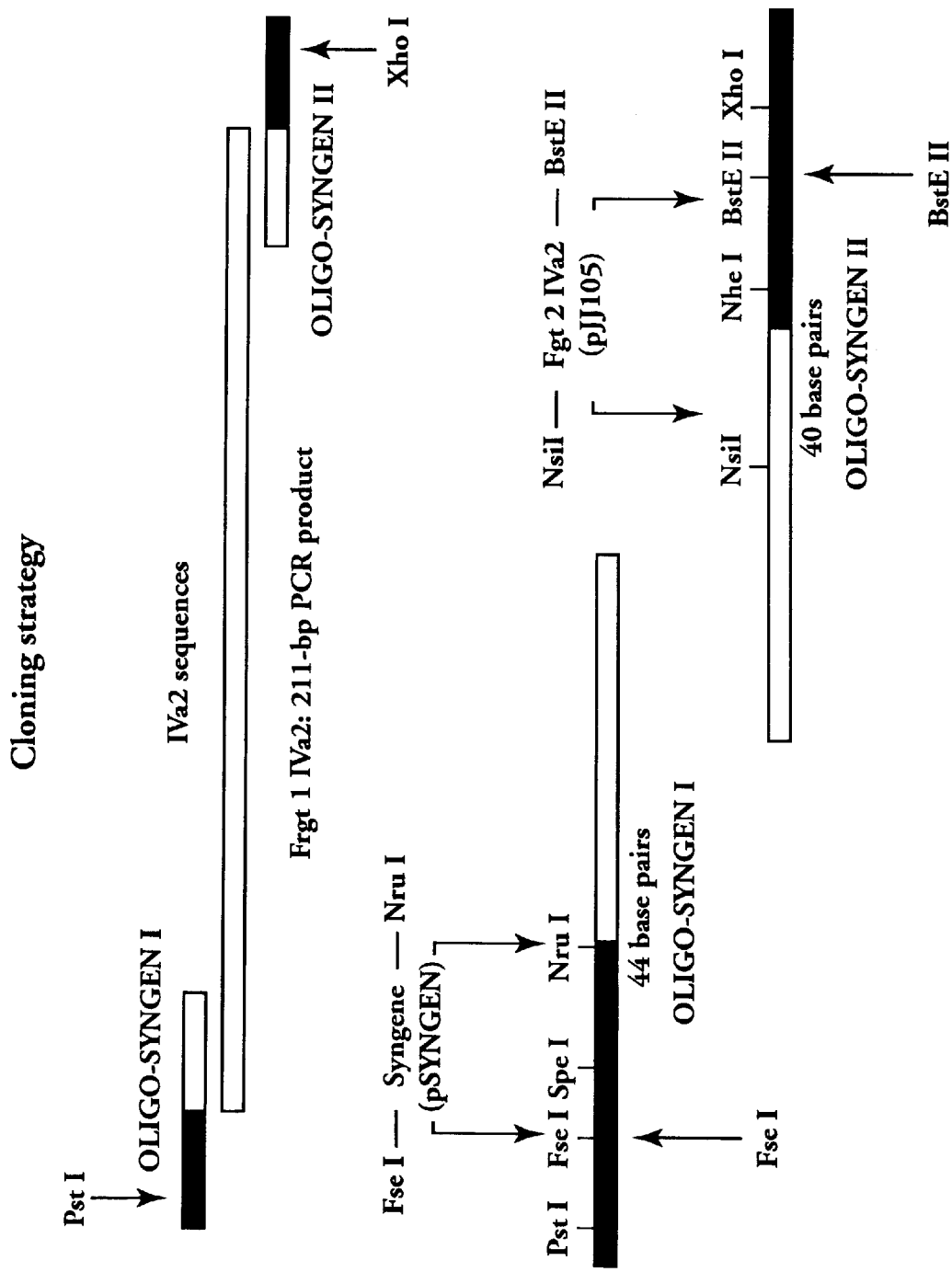

FIG. 6: Construction of the defective virus carrying the syngen as a replacement for the natural region.

FIG. 7: Structure and restriction map of the oligonucleotides Oligosyngen I and Oligosyngen II.

FIG. 8: Natural nucleotide sequence and degenerate sequence of the pIX gene (SEQ ID NO: 1), and corresponding amino acid sequence SEQ ID NO:2.

FIG. 9: Natural nucleotide sequence and degenerate sequence of the Iva2 gene (SEQ ID NO:3), and corresponding amino acid sequence SEQ ID NO:4.

Figure 10A:
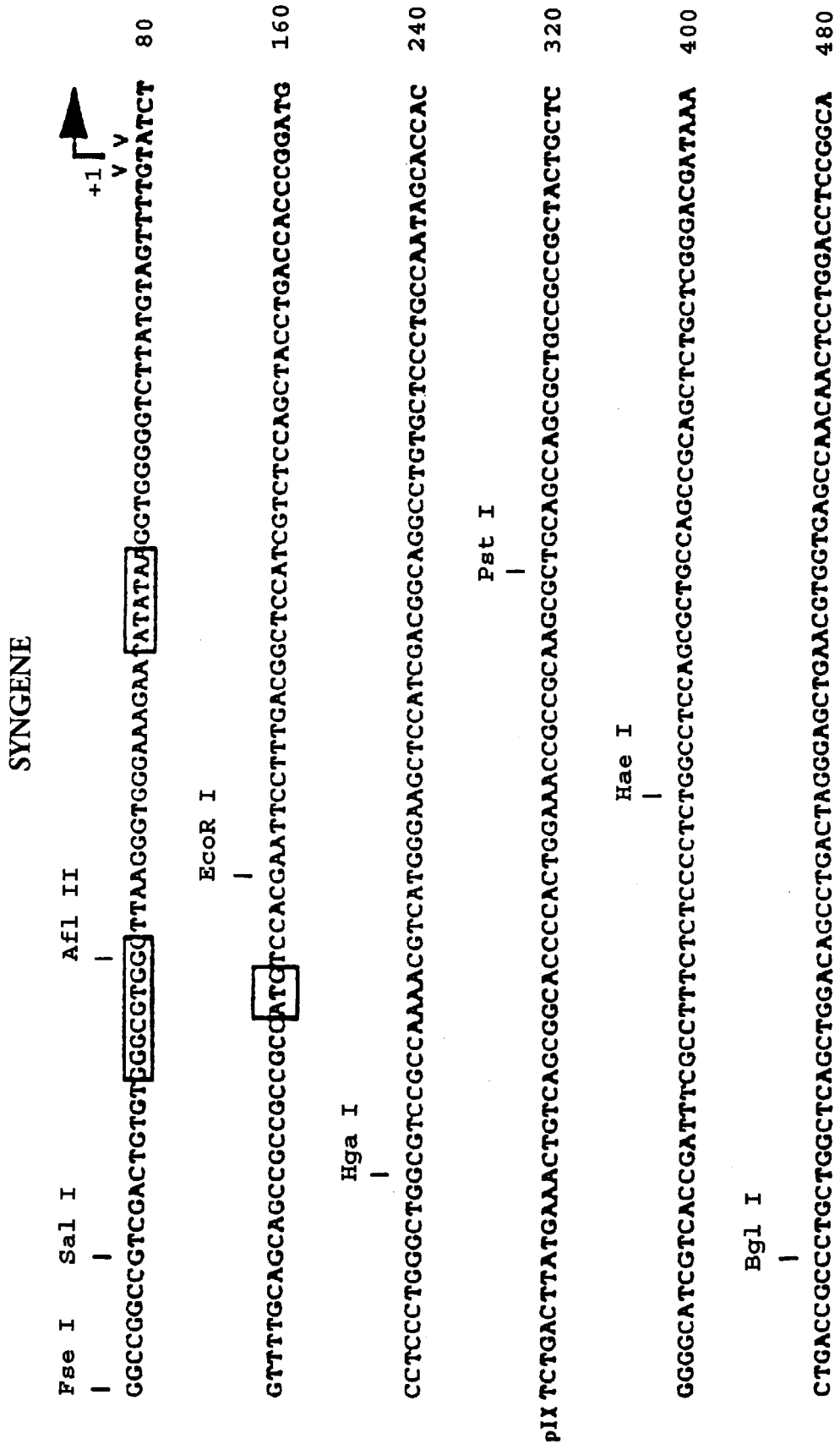

FIG. 10: Nucleotide sequence of syngen #1 (SEQ ID NO:5)

Figure 11:
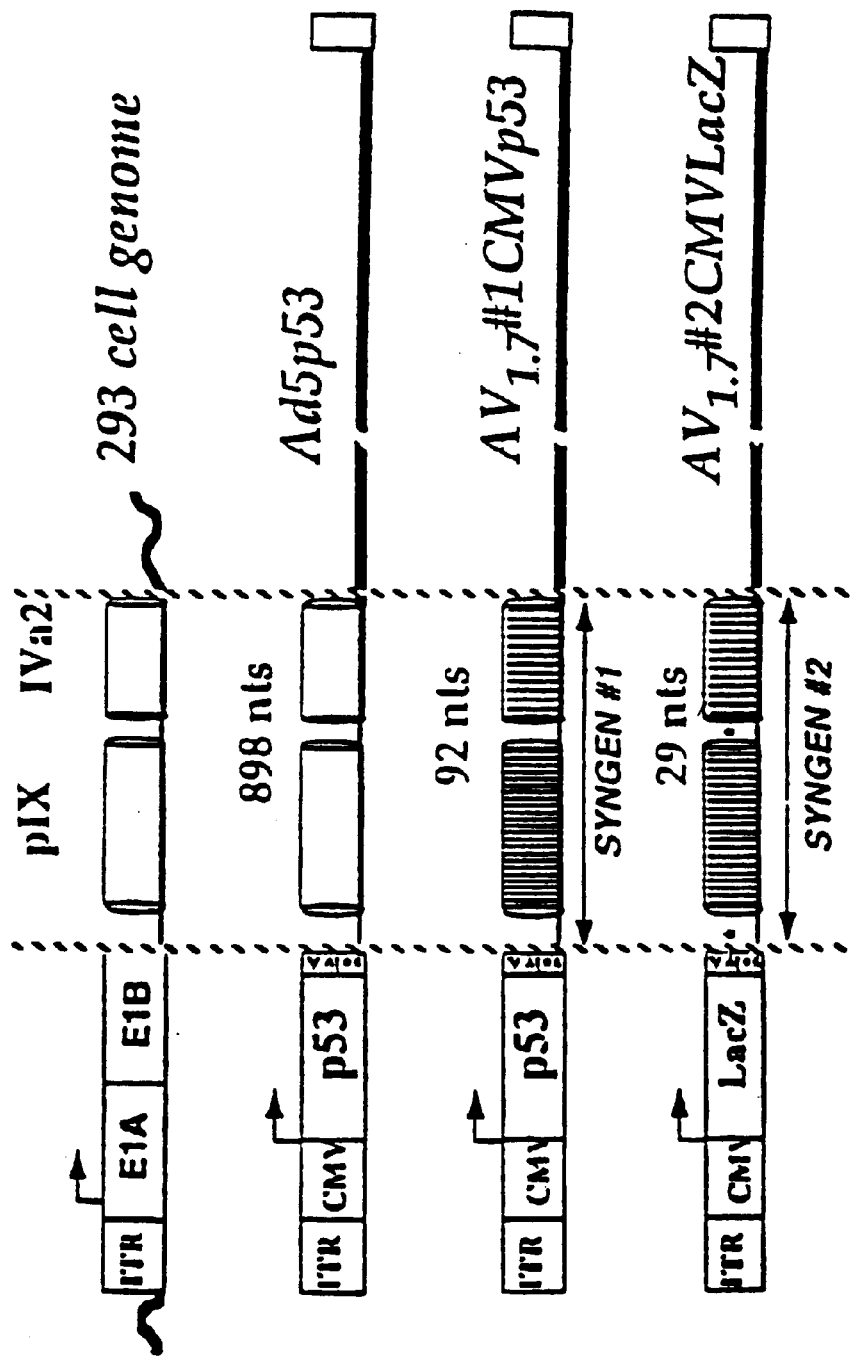

FIG. 11: Schematic representation of the homologies between the genome of the 293 cell and the recombinant Ad5 vectors. The vector Ad5p53 has a continuous sequence homology of 898 nucleotides with the genome of the 293 cell, downstream of the E1 region. The introduction of point mutations reduces the maximum length of continuous homology to 92 nucleotides in the case of syngen #1 (AV 1.7 #1 CMV p53) and 29 nucleotides in the case of syngen #2 (AV 1.7 #2 CMV lac Z).

FIG. 12: RCA detection for vectors ad5p53 and AV 1.7 #1 p53 after 7 successive amplifications in 293-line cells.

GENERAL MOLECULAR BIOLOGY TECHNIQUES

The methods conventionally used in molecular biology, such as preparative extractions of plasmid DNA, centrifugation of plasmid DNA in a caesium chloride gradient, agarose or acrylamide gel electrophoresis, purification of DNA fragments by electroelution, extraction of proteins with phenol or phenol/chloroform, ethanol or isopropanol precipitation of DNA in saline medium, transformation in *Escherichia coli*, etc., are well known to persons skilled in the art and are widely described in the literature [Maniatis T., et al., "Molecular Cloning, a Laboratory Manual", Cold Spring Harbor Laboratory, Cold Spring Harbor, N.Y., 1982; Ausubel F. M., et al., (eds), "Current Protocols in Molecular Biology", John Wiley & Sons, New York, 1987].

The plasmids pIC-20R (Invitrogen) and pBS (Stratagen) are of commercial origin.

For ligations, the DNA fragments can be separated according to their size by agarose or acrylamide gel electrophoresis, extracted with phenol or with a phenol/chloroform mixture, precipitated with ethanol and then incubated in the presence of T4 phage DNA ligase (Biolabs) according to the supplier's recommendations.

Filling of the protruding 5' ends can be carried out with the Klenow fragment of *E. coli* DNA polymerase I (Biolabs) according to the supplier's specifications. Destruction of the protruding 3' ends is carried out in the presence of T4 phage DNA polymerase (Biolabs) used according to the manufacturer's recommendations. Destruction of the protruding 5' ends is carried out by a controlled treatment with S1 nuclease.

Site-directed mutagenesis in vitro by synthetic oligodeoxynucleotides can be carried out according to the method developed by Taylor et al., [Nucleic Acids Res. 13 (1985) 8749–8764] using the kit distributed by Amersham.

Enzymatic amplification of DNA fragments by the so-called PCR technique [polymerase-catalysed Chain Reaction, Saiki R. K. et al., Science 230 (1985) 1350–1354; Mullis K. B. and Faloona F. A., Meth. Enzym. 155 (1987) 335–350] can be carried out using a DNA thermal cycler (Perkin Elmer Cetus) according to the manufacturer's specifications.

Verification of the nucleotide sequences can be carried out by the method developed by Sanger et al., [Proc. Natl. Acad. Sci. USA, 74 (1977) 5463–5467] using the kit distributed by Amersham.

Cell Lines Used 293 human embryonic kidney line (Graham et al., J. Gen. Virol. 36 (1977) 59). This line contains in particular, integrated into its genome, the left-hand portion of the genome of the Ad5 human adenovirus (12%).

EXAMPLE 1

Homologous Recombination In the Adenovirus

The observation that the adenovirus genome can undergo genetic recombination events was reported more than 25 years ago (Williams and Ustacelibi, 1971). However, the mechanisms underlying these recombination events are relatively unknown. It has been proposed that the recombination and replication may be closely linked, and certain data are in favour of a model of recombination in which the replication would produce the specific substrates which are required for the frequent recombination events observed during the infection by the adenovirus. One of the questions is to know whether or not viral or cellular proteins participate in the formation of the recombination intermediates and in their resolution into final recombinant products. In this respect, none of the viral genes tested were shown to be involved in the recombination events: E1b, E4, E1a, E3 (Epstein, 1991; Weinberg et al., 1986; Young, 1995). Similarly, no cellular protein was demonstrated as being involved. Two models were finally proposed for the mechanism of recombination in the viral genome, both predicting the formation of widespread heteroduplexes (Ahern et al., 1991; Young, 1995).

The regions responsible for the homologous recombination between the defective genome and the cell line have been located in particular in the pIX and IVa2 genes of the adenovirus genome. The structure of this region, which is present in the defective genome, is represented in FIG. 2.

Modifications of the sequence of the adenovirus genome, which is involved in the recombination with the cellular genome, were carried out. More specifically, the natural Sequence of the pIX and IVa2 genes was modified by introducing silent mutations which make it possible to reduce the homology with the natural sequence without affecting the structure of the expression products of these genes.

The sequence obtained, referred to as syngen, is used as a replacement for the corresponding natural sequence of the adenovirus, to construct the defective vector.

1. Identification of the Regions Responsible For the Recombination

Mapping studies have shown that the portion of the adenovirus genome which is present in the genome of the 293 cells corresponds to the left-hand portion of the adenoviral genome and represents about 12% of it, i.e. about 4300 pb (Aiello et al., 1979; Spector et al., 1983). The Applicant has carried out additional mapping experiments by PCR and has shown that position 4420 is present in the genome of 293. This position 4420 was chosen for the following experiments as the right-hand limit of the zone of homology and thus the right-hand limit of the syngen. For technical cloning reasons the modified fragment will stretch as far as position 4445 where a cloning site has been introduced.

The left-hand end of the syngen was chosen within the regulatory elements for the expression of the pIX gene, and more particularly at position -56 of the pIX gene. It has in fact been shown that the pIX gene promoter could be reduced to a 56-nucleotide region. The activity of this region, which contains the SP1 binding site and the TATA box, is comparable to that of the 250-nucleotide fragment (Babiss et al., 1991; Matsu et al., 1989).

The zone of homology was thus determined as stretching from position 3520 to position 4445 of the genome of the defective virus (see FIG. 2).

2. Design of Modified Sequences

A table of codon use in the genome of the Ad5 adenovirus was prepared by the Applicant and used to determine the optimum codon use for the expression of the viral proteins. This table was obtained by combining the data obtained after the analysis of 10 proteins of the adenovirus: pIX, Hexon, pIII, pVII, 52–55k, pPol, pTP, DBP, 23K and 19k (see table). The results obtained were then compared with a table of human codon use obtained by analysis of 1952 genes present in the Genbank base using the GCG program.

An order of preference for the use of the codons was then established for modifying the codon sequence of the pIX and IVa2 genes:

When the codon used in the natural sequence is not the preferred codon, it is used in the syngen.

When the codon used in the natural sequence is the preferred codon, it is then the second-preferred codon which is used.

In certain cases, for example for introducing a restriction site, the third-preferred codon can be used, in particular when its frequency is sufficiently close to that of the second-preferred codon.

The table below indicates the frequency of codon use in humans and in the adenovirus (ADV5) with the order of preference in humans (column A), the order of preference for the adenovirus (column B) and the choice retained for the synthesis of the syngen (column C).

TABLE 1

Frequency of codon use

|   |     |     | ADV5 |       | Human |        | A | H | C |
|---|-----|-----|------|-------|-------|--------|---|---|---|
| F | TTT | Phe | 2.3  | 54.2% | 1.5   | 43.0%  | 1 | 2 | — |
| F | TTC |     | 1.9  | 45.8% | 2.1   | 57.0%  | 2 | 1 | — |
| L | TTA | Leu | 0.1  | 1.4%  | 0.6   | 6.0%   | 6 | 6 | 6 |
| L | TTG |     | 1.2  | 14.2% | 1.1   | 12.0%  | 4 | 4 | 4 |
| L | CTT | Leu | 1.3  | 15.6% | 1.1   | 12.0%  | 3 | 3 | 3 |
| L | CTC |     | 1.7  | 20.5% | 1.9   | 20.0%  | 2 | 2 | 2 |
| L | CTA |     | 1.1  | 12.6% | 0.6   | 7.0%   | 5 | 5 | 5 |
| L | CTG |     | 3    | 35.1% | 4     | 43.0%  | 1 | 1 | 1 |
| I | ATT | Ile | 1.3  | 34.6% | 1.5   | 35.0%  | 2 | 2 | 2 |
| I | ATC |     | 1.6  | 43.8% | 2.3   | 52.0%  | 1 | 1 | 1 |
| I | ATA |     | 0.8  | 21.6% | 0.7   | 14.0%  | 3 | 3 | 3 |
| M | ATG | Met | 2.6  | 100.0%| 2.2   | 100.0% |   |   |   |
| V | GTT | Val | 0.8  | 13.1% | 1     | 17.0%  | 3 | 3 | 3 |
| V | GTC |     | 1.4  | 22.2% | 1.5   | 25.0%  | 2 | 2 | 2 |
| V | GTA |     | 0.8  | 12.5% | 0.6   | 10.0%  | 4 | 4 | 4 |
| V | GTG |     | 3.3  | 52.5% | 2.9   | 48.0%  | 1 | 1 | 1 |
| Y | TAT | Tyr | 0.8  | 21.6% | 1.2   | 41.7%  | 2 | 2 | 2 |
| Y | TAC |     | 3    | 78.4% | 1.7   | 58.3%  | 1 | 1 | 1 |
| * | TAA | end |      |       | 0.1   | 23.8%  |   |   |   |
| * | TAG |     |      |       | 0.1   | 16.7%  |   |   |   |
| H | CAT | His | 0.5  | 21.3% | 1.4   | 59.3%  | 2 | 1 | — |
| H | CAC |     | 1.7  | 78.7% | 1     | 40.7%  | 1 | 2 | — |
| Q | CAA | Gln | 1.1  | 27.4% | 1.2   | 26.7%  | 2 | 2 | 2 |
| Q | CAG |     | 3    | 72.6% | 3.3   | 73.3%  | 1 | 1 | 1 |
| N | AAT | Asn | 1.2  | 24.5% | 1.6   | 43.5%  | 2 | 2 | 2 |
| N | AAC |     | 3.6  | 75.5% | 2.1   | 56.5%  | 1 | 1 | 1 |
| K | AAA | Lys | 1.4  | 35.2% | 2.2   | 39.8%  | 2 | 2 | 2 |
| K | AAG |     | 2.5  | 64.8% | 3.4   | 60.2%  | 1 | 1 | 1 |
| D | GAT | Asp | 1.6  | 29.2% | 2.1   | 44.2%  | 2 | 2 | 2 |
| D | GAC |     | 3.9  | 70.8% | 2.7   | 55.8%  | 1 | 1 | 1 |
| E | GAA | Glu | 2.4  | 37.0% | 2.8   | 41.5%  | 2 | 2 | 2 |
| E | GAG |     | 4.1  | 63.0% | 3.9   | 58.5%  | 1 | 1 | 1 |
| S | TCT | Ser | 0.8  | 11.7% | 1.4   | 18.0%  | 4 | 3 | 3 |
| S | TCC |     | 1.7  | 25.9% | 1.7   | 23.2%  | 2 | 2 | 2 |
| S | TCA |     | 0.6  | 9.6%  | 1.1   | 14.7%  | 5 | 4 | 4 |
| S | TCG |     | 0.9  | 13.6% | 0.4   | 5.9%   | 3 | 6 | 5 |
| P | CCT | Pro | 1.2  | 18.4% | 1.8   | 29.0%  | 4 | 2 | 2 |
| P | CCC |     | 2.7  | 39.9% | 2.1   | 33.0%  | 1 | 1 | 1 |
| P | CCA |     | 1.3  | 18.7% | 1.7   | 27.0%  | 3 | 3 | 3 |
| P | CCG |     | 1.5  | 23.0% | 0.1   | 11.0%  | 2 | 4 | 4 |
| T | ACT | Thr | 1.1  | 17.7% | 1.3   | 23.0%  | 2 | 3 | 2 |
| T | ACC |     | 3.3  | 55.0% | 2.2   | 38.0%  | 1 | 1 | 1 |
| T | ACA |     | 0.8  | 12.8% | 1.5   | 27.0%  | 4 | 2 | 4 |
| T | ACG |     | 0.9  | 14.5% | 0.1   | 12.0%  | 3 | 4 | 3 |
| A | GCT | Ala | 1.2  | 13.7% | 2     | 28.0%  | 3 | 2 | 2 |
| A | GCC |     | 4    | 45.7% | 2.8   | 40.0%  | 1 | 1 | 1 |
| A | GCA |     | 1.1  | 12.6% | 1.6   | 22.0%  | 4 | 3 | 3 |
| A | GCG |     | 2.4  | 27.9% | 0.7   | 10.0%  | 2 | 4 | 4 |
| C | TGT | Cys | 0.3  | 21.5% | 1     | 41.8%  | 2 | 2 | 2 |
| C | TGC |     | 1.1  | 78.5% | 1.4   | 58.2%  | 1 | 1 | 1 |
| * | TGA | end |      |       | 0.3   | 11.9%  |   |   |   |
| W | TGG | Trp | 1.3  | 100.0%| 1.5   | 100.0% |   |   |   |
| R | CGT | Arg | 0.8  | 10.4% | 0.5   | 9.3%   | 3 | 6 | 6 |
| R | CGC |     | 4.1  | 52.4% | 1.1   | 19.4%  | 1 | 3 | 1 |
| R | CGA |     | 0.6  | 7.0%  | 0.6   | 10.0%  | 5 | 5 | 5 |
| R | CGG |     | 1.1  | 13.9% | 1     | 18.6%  | 2 | 4 | 2 |
| S | AGT | Ser | 0.4  | 6.6%  | 1     | 13.6%  | 6 | 5 | 6 |
| S | AGC |     | 2.1  | 32.6% | 1.9   | 24.7%  | 1 | 1 | 1 |
| R | AGA | Arg | 0.5  | 6.2%  | 1.2   | 21.0%  | 6 | 2 | 4 |
| R | AGG |     | 0.8  | 10.2% | 1.2   | 21.7%  | 4 | 1 | 3 |
| G | GGT | Gly | 1    | 17.7% | 1.4   | 18.3%  | 4 | 4 | 4 |
| G | GGC |     | 2.4  | 41.3% | 2.5   | 33.2%  | 1 | 1 | 1 |
| G | GGA |     | 1.3  | 21.5% | 1.9   | 25.7%  | 2 | 2 | 2 |
| G | GGG |     | 1.1  | 19.4% | 1.7   | 22.8%  | 3 | 3 | 3 |

In a first specific syngen example (syngen #1), the following modifications were introduced:

In the pIX promoter: the sequence was reduced as much as possible: the fragment retained contains only 56 nucleotides, instead of 135 nucleotides in the original vector. An additional modification can be introduced by modification of the 9 nucleotides situated between the SP1 binding site and the TATA box.

In the pIX gene: all the positions were degenerated, when that was possible, according to the rule defined above, without modification of the resulting amino acid Sequence (SEQ ID NO:2). The comparison of the natural sequence and the degenerate sequence, as well as the structure of the expression product of these sequences, are presented in FIG. 8. According to another strategy, only one position (bp) in 10 is degenerated. Still according to an alternative strategy, only one position in 20 [lacuna].

In the interval region between pIX and IVa2: the sequence of this region, of 59 nucleotides, was not modified in this example.

In the IVa2 gene: the coding sequence of the IVa2 gene was degenerated according to the rule defined above, every 20 bp, without modification of the resulting amino acid sequence (see SEQ ID NO:3 and SEQ ID NO:4). The natural sequence, the degenerate sequence and the resulting amino acid sequence are presented in FIG. 9. According to another strategy, one position (bp) in 10 is degenerated or even all the positions, still without modification of the resulting amino acid sequence.

The structure of syngen #1 is described schematically in FIG. 2. The sequence of syngen #1 is represented in FIG. 10 and by the sequence SEQ ID NO:5.

Another syngen example is provided by syngen #2 in which:

The sequence of the pIX gene promoter was replaced with a modified sequence as described in SEQ ID NO:10.

The sequence of the pIX gene was replaced according to the sequence described in SEQ ID NO:6 without modification of the resulting amino acid sequence SEQ ID NO:7.

The sequence of the IVa2 was replaced according to the sequence described in SEQ ID NO:8 without modification of the resulting amino acid sequence SEQ ID NO:9.

The polyadenylation region was replaced with the region which carries out the same functions in the adenovirus of type 7 (Ad 7); an adenovirus of the subgroup B which is used as a vector for gene transfer (Abrahamsen et al., 1997, J. Virol. 71, 8946–8951). This sequence is described in the sequence SEQ ID NO:11.

The entire modified sequence is called syngen #2 and is represented by the sequence SEQ ID NO:12.

3. Verification of the Sequence of the Syngens

The basic characteristics of the natural and syngen sequences are verified by data-processing analysis. The aim of this verification is to investigate the possible presence, in the syngens, of specific structures, and in particular:

of donor or acceptor splice sites (SpliceView and/or Splice Net programs)

of polyadenylation sites (Hcpolya program)

of potential sites for binding of transcriptional factors (Transfac program)

of regions capable of forming specific secondary structures such as direct repeats, hairpin (Sigscan program, BNL), including in the corresponding RNAs (RNA folding)

of consensus sites such as CHI or M26.

When such sequences are identified, the corresponding bases can optionally be replaced according to the strategy defined in 2, above.

4. Construction of Defective Viruses Carrying Syngen #1 As a Replacement for the Corresponding Natural Region 1. Starting material:

Syngen #1 (SEQ ID NO:5)

The oligonucleotides Syngen I and Syngen II corresponding respectively to the 5' and 3' ends of syngen #1 are given in FIG. 7.

Plasmid pJJ105 (FIG. 3)

Plasmid pJJ110 (FIG. 4)

Plasmid pIC-20R (Invitrogen)

Plasmid pSyngen: syngen cloned into pBS (Stratagene)

2. Construction of the defective viral genome

The construction strategy is described in FIG. 6.

The plasmid pJJ110 is digested with XbaI, and the resulting 4.8 and 5.0 kb XbaI fragments are ligated to form the plasmid pJJ201. The plasmid pJJ201 is then digested with BstEII and XmaI, filled in and ligated to form the plasmid pJJ202. The two sites BstEII and XmaI are conserved.

The PCR amplification product corresponding to fragment 1 of the IVa2 gene (Fgt1 for IVa2, FIG. 6) is generated using the oligo syngen I and the oligo syngen II and the plasmid pJJ105 as a matrix.

Sequence of the oligo syngen I (SEQ ID NO:13)

AACTGCAGGCCGGCCACTAGTCGCGAT-
GTTCCCAGCCATATCCC

Sequence of the oligo syngen II (SEQ ID NO:14)

CCGCTCGAGGTGACCGCTAGCCATTATGGACGAATGC

The amplified fragment is inserted into the SmaI site of pIC-20R to generate pJJ203. A contiguous fragment of the IVa2 gene from the plasmid pJJ105 (Fragment 2, identified Fgt2 Iva2 in FIG. 6) is excised with NsiI/BstEII and then inserted at the corresponding sites of pJJ203 to generate pJJ204. The syngen is then digested with FseI/NruI (FIG. 6) and inserted between the corresponding sites of pJJ204 to generate pJJ205.

The complete fragment (syngen#1-Fgt1+2 IVa2) of pJJ205 is digested with Sse 8387I/BstEII and inserted at the corresponding sites in pJJ202 to generate pJJ206 (FIG. 5).

This fragment is then used to prepare a prokaryotic plasmid comprising a modified adenovirus genome (defective for E1 and optionally E3) containing syngen #1, according to the method described in Crouzet et al., (PNAS (94) 1414–1419 (1997)). The plasmid obtained is then transfected into the 293-line cells to produce the corresponding viruses.

An experiment was conducted to compare the capacity of RCAs (replication-competent adenoviruses) to appear during the propagation, with the aid of the 293 cell, of two viruses AV1.7#1CMVp53 and Ad5CMVp53.

A vector (AV1.7 #1CMVp53) equipped with the sequence SEQ ID NO: 3 (syngen #1) and armed with a p53 expression cassette (CMV-p53-polyASV40) was constructed according to Crouzet et al. (PNAS (94) 1414–1419 (1997)).

Ad5CMVp53 contains the regions of pIX-IVa2 of the Ad5 (unmodified). The p53 expression cassette is isogenic for the two viruses. The two viruses AV1.7#1CMVp53 and the Ad5CMVp53 have similar productivity in the 293 cell. For each of the viruses, 5 plaques were purified on the 293 cell. The 2×5 plaques were amplified over 7 successive passages.

On completion of these amplifications, the 2×5 samples of passage 7 were analysed in an RCA detection experiment. The experiment was carried out in triplicate. The results are presented in FIG. 12.

The method for detecting the RCAs is a quantitative method which makes it possible to count the plaques, the number of which corresponds to the number of RCAs in the dose of the test sample. A given dose of virus of a sample (conventionally $3 \times 10^{10}$ vp) is used to infect a cell lawn of a non-transcomplementing cell (i.e. which does not express E1, in this instance the A549 cell) onto which is placed a layer of agar. After 14 days, plaque formation is observed in the lawn when the starting infecting dose contains RCAs.

The results of the RCA detection experiment conducted in triplicate are: 0 RCA for AV1.7#1CMVp53 and 6 RCA for the Ad5CMVp53. This result is statistically significant when a statistical method of comparison which involves the conditional probability of the observation is used. A statistically significant improvement is observed in favour of the vector AV1.7#1CMVp53, in terms of reduction of the appearance of RCA during the propagation in the 293 cell of this vector compared to a conventional vector. This set of results makes it possible to show that the presence of the syngen does not affect the titres of virus produced, and that the batches of virus comprising syngen #1 are free of contamination by RCA.

5. Functionality of Defective Viruses Carrying Syngen #2 As a Replacement for the Corresponding Natural Region In the same way, a similar vector was constructed with syngen #2 and armed with a LacZ expression cassette (CMV-LacZ): AV1.7#2CMVlacZ. The productivity of this vector was compared to that of a vector armed with a LacZ cassette (RSV LacZ), whose pIX and Iva2 regions have not been modified (sequence of the wild-type Ad5): AV1.0RSVlacZ. The productivity of the two vectors AV1.7#2CMVlacZ and AV1.0RSVlacZ was tested in parallel in 293-line cells. The results are presented in the table below.

|  | AV1.7#2CMVlacZ | AV1.0RSVlacZ |
|---|---|---|
| Titre Stock 1 (vp/ml) | $1.12 \ 10^{12}$ | $1.50 \ 10^{12}$ |
| Titre Stock 2 (vp/ml) | $1.52 \ 10^{12}$ | $1.82 \ 10^{12}$ |
| Productivity (vp/cell) tested on Stock 2 | 10133 | 12133 |
| Productivity (tdu/cell) tested on Stock 2 | 203 | 207 |

These results show that syngen #2 having a homology which is more reduced than syngen #1 and which contains, besides silent mutations in the pIX and Iva2 genes, modifications in the noncoding regions (i.e. in the pIX gene promoter and overlapping polyadenylation sequences of pIX and Iva2); such a syngen, when it is introduced as a replacement for the wild-type sequences of the adenovirus of type 5, turns out to be viable and to give a high productivity.

6. Construction of Defective Viruses In Which Only the Natural Sequence of the pIX Gene Is Replaced With the Degenerate Sequence Described in SEQ ID NO: 1 and the Portion of the Homologous Region Which Corresponds To the IVa2 Gene Is Moved Into the E4 Region According to another embodiment variant, only the natural sequence of the pIX gene is replaced with the degenerate sequence described in SEQ ID NO: 1 and the portion of the homologous region which corresponds to the IVa2 gene is moved into the E4 region. The cloning of the Iva2 gene has been described in application WO 96/10088 included herein by way of reference.

A first plasmid, named pIE11, was constructed, and contains the 3 SEQ ID NO: 15 regions below cloned into a plasmid colE1 which carries the genes KanR and SacB:

A PCR product made on Ad5 with the primers:

5'atcgatcgATAACAGTCAGCCTTACC-3' and

5'-agctgaattcCATCATCAATAATATACC-3' this PCR product contains the right ITR and the E4 promoter as far as the ATG of orf1, not inclusive (nucleotides 35525 to 35937)

the cDNA of the IVa2 gene described in patent application WO/9610088.

the XcmI-EcoRV fragment of Ad5 which contains the sequences required for the splicing of orf6 of E4 and the coding sequence of orf6 as far as the EcoRV site.

The IVa2 CDNA in the plasmid pIE11 is preceded by an excess ATG. This site is destroyed in the plasmid pIE11 by site-directed mutagenesis with the aid of a Transformer Site-directed mutagenesis kit from Clontech, to form the plasmid pIE12 in which this ATG has been destroyed.

The plasmid pIE12c derive from the plasmid pIE12 contains an adenovirus 5 genome modified in the following way: moving the IVa2 gene from its natural locus to the E4 region, replacing the orfs 1 to 4 of E4 to the benefit of the IVa2 CDNA, deleting E3, inserting an RSV-lacZ cassette in place of E1. The plasmid pIE12c was obtained by recombination with the plasmid pXL2788βGal as described in application WO 96/10088, using the technology described in Crouzet et al., (PNAS (94) 1414–1419 (1997)) included herein by way of reference.

After enzymatic digestion with PacI, the plasmid pIE12c was transfected into 293 and the virus obtained was amplified. It is observed that the restriction profile of the virus AdIE12 is that which is expected.

The analyses carried out on the batches of virus produced make it possible to show that the presence of the degenerate sequence of the pIX gene in place of the natural sequence and the movement of the IVa2 gene into the E4 region do not affect the titres of virus produced and that the batches of virus are free of contamination with RCA when these batches are tested under the conditions described above.

BIBLOGRAPHIC REFERENCES

Ahern et al. (1991) PNAS 88: 105
Aiello et al. (1979) Virol. 94: 460
Babiss and Vales (1991) J. Virol. 65: 598
Epstein (1991) J. Virol. 65: 4475
Gangloff et al. (1994) Experientia 50: 261
Holliday (1964) Genet. Res. 5: 282–304
Jeong-Yu and Carroll (1992) Mol. Cell. Biol. 12(1): 112–9
Lin et al. (1990) Mol Cell. Biol. 10(1): 103–12
Matsui (1989) Mol. Cell. Biol. 9: 4265
Meselson M., Radding C. (1975) Proc. Natl. Acad. Sci. USA, 80: 358–361
Spector (1983) Virol. 130: 533
Szostak et al. (1963) Cell 33: 25–35
Waldman and Liskay (1987) PNAS 84(15) 5340–4
Weinberg (1986) J. Virol, 57; 833
Williams and Ustacelibi (1971) J. Gen. Virol. 13: 345
Young (1995) Current Topics in Microbiol. And Immunol. 199: 89

What is claimed is:

1. A method for reducing the frequency of intra- or intermolecular homologous recombination events between a chromosomal nucleic acid and an extrachromosomal nucleic acid of a cell, wherein the method comprises introducing into the cell comprising the chromosomal nucleic acid that encodes a complementing function of a defective adenovirus, an extrachromosomal nucleic acid which comprises a genome of the defective adenovirus, wherein at least one of the nucleic acids is modified in such a way as to reduce its homology with the other nucleic acid.

2. The method according to claim 1, wherein the modified nucleic acid comprises a coding sequence that is degenerated.

3. The method according to claim 1, wherein the degeneracy is produced as a function of codon use of the complementing cell.

4. The method according to claim 1, wherein the modified nucleic acid is degenerated in a proportion of 1 base pair at least every 20 base pairs.

5. The method according to claim 4, wherein the modified nucleic acid is degenerated in a proportion of 1 base pair at least every 10 base pairs.

6. The method according to claim 1, wherein the modified nucleic acid is degenerated over all possible positions.

7. The method according to claim 1, wherein the chromosomal nucleic acid comprises an E1 region of an adenovirus genome, as well as a flanking region, and the extrachromosomal nucleic acid comprises a genome of an adenovirus which is defective for an E1 region.

8. The method according to claim 7, wherein the genome of the adenovirus defective for the E1 region is degenerated in a pIX gene.

9. The method according to claim 8, wherein the genome of the adenovirus defective for the E1 region is further degenerated in an IVa2 gene.

10. A method for preparing a defective recombinant adenovirus comprising introducing into a complementing cell comprising a chromosomal nucleic acid that encodes a complementing function of the defective recombinant adenovirus, a defective recombinant adenovirus genome that comprises a deletion of an E1 region and a degeneracy in pIX and/or IVa2 genes.

11. A defective recombinant adenovirus whose genome comprises at least one region whose sequence is modified in such a way as to reduce the frequency of an intermolecular homologous recombination event with a chromosomal nucleic acid which encodes a complementing function of the defective recombinant adenovirus, wherein the sequence is modified in such a way as to reduce its homology with the chromosomal nucleic acid.

12. The defective recombinant adenovirus according to claim 11, wherein the modified sequence comprises a coding region that comprises a degenerated pIX gene.

13. The defective recombinant adenovirus according to claim 12, wherein the degenerated pIX gene comprises a nucleic acid sequence of SEQ ID NO: 1.

14. The defective recombinant adenovirus according to claim 12, wherein the defective recombinant adenovirus comprises an IVa2 gene is present in a genomic position other than its original position.

15. The defective recombinant adenovirus according to claim 14, wherein the IVa2 gene is positioned in an E4 region.

16. The defective recombinant adenovirus according to claim 11, wherein the modified sequence comprises pIX and IVa2 genes.

17. The defective recombinant adenovirus according to claim 16, wherein the modified sequence comprises a nucleic acid sequence of SEQ ID NO: 5.

18. The defective recombinant adenovirus according to claim 11, further comprising a deletion of an E1 region.

19. A cell comprising a) a chromosomal nucleic acid that encodes a complementing function of a defective recombinant adenovirus, and b) an extrachromosomal nucleic acid comprising a genome of the defective recombinant adenovirus, wherein at least one of the nucleic acids is modified in such a way as to reduce its homology with the other nucleic acid.

* * * * *

UNITED STATES PATENT AND TRADEMARK OFFICE
CERTIFICATE OF CORRECTION

PATENT NO.    : 6,410,298 B1
DATED         : June 25, 2002
INVENTOR(S)   : Joel Crouzet et al.

It is certified that error appears in the above-identified patent and that said Letters Patent is hereby corrected as shown below:

<u>Column 30,</u>
Line 29, delete "is".

Signed and Sealed this

Thirty-first Day of December, 2002

JAMES E. ROGAN
*Director of the United States Patent and Trademark Office*